United States Patent
Ziv et al.

(10) Patent No.: US 6,602,852 B1
(45) Date of Patent: Aug. 5, 2003

(54) BASIC PEPTIDES AND PHARMACEUTICAL COMPOSITIONS CONTAINING SAME

(75) Inventors: Ilan Ziv, Kfar-Sava (IL); Anat Shirvan, Herzilya (IL)

(73) Assignee: NST NeuroSurvival Technologies, Ltd. (IL)

( * ) Notice: Subject to any disclaimer, the term of this patent is extended or adjusted under 35 U.S.C. 154(b) by 0 days.

(21) Appl. No.: 09/763,548

(22) PCT Filed: Aug. 23, 1999

(86) PCT No.: PCT/IL99/00456

§ 371 (c)(1),
(2), (4) Date: Feb. 23, 2001

(87) PCT Pub. No.: WO00/11026

PCT Pub. Date: Mar. 2, 2000

(30) Foreign Application Priority Data

Aug. 24, 1998 (IL) ................................................. 125908

(51) Int. Cl.[7] .................. A61K 38/17; C07K 14/47; G01N 33/68
(52) U.S. Cl. .................. 514/12; 424/1.69; 424/9.1; 424/9.341; 424/9.6; 514/2; 514/13; 514/14; 514/15; 514/16; 530/300; 530/324; 530/326; 530/327; 530/328; 530/329
(58) Field of Search ................. 424/1.69, 9.1, 424/9.322, 9.323, 9.34, 9.341, 9.4, 9.411, 9.6; 514/2, 12, 13, 14, 15, 16, 17, 18, 19, 20; 530/324, 325, 326, 327, 328, 329, 330, 331, 334, 345; 435/29; 548/338.1, 496; 562/433, 439, 440, 443, 444, 445, 448, 450, 553, 561, 562, 563, 564, 567, 570, 575

(56) References Cited

U.S. PATENT DOCUMENTS 3,701,433 A  10/1972  Krakauer et al. ........... 210/436
3,935,111 A   1/1976  Bentley ....................... 210/446
4,283,289 A   8/1981  Meyst et al. ................. 210/448

(List continued on next page.)

FOREIGN PATENT DOCUMENTS

| EP | 0 210 412 A | 2/1987 |
| EP | 0 755 516 B1 | 12/1997 |
| IL | 125908 | 8/1998 |

(List continued on next page.)

OTHER PUBLICATIONS

Sestier et al., "Use of Annexin V–Ferrofluid to Enumerate Erythrocytes Damaged in Various Pthologies or During Storage In Vitro", Nov. 1995, pp. 1141–1146, C R Acad Sci III, 318:11.

Halbreich et al., "Biomedical Applications of Maghemite Ferrofluid", May–Jun. 1998, pp. 379–390, Biochimie, 80(5–6).

(List continued on next page.)

Primary Examiner—Jeffrey E. Russel

(57) ABSTRACT

The present invention relates to an NST300 compound of general formula (I): comprising the following components: X1—[(X3)a/(X4)b] in which X1 represents a fatty acid or prenyl group; and X3 represents a domain of positively charged amino acids; and X4 represents a domain containing aromatic amino acids; and a stands for an integer of 1–8; and b stands for an integer of 1–8. The invention relates also to pharmaceutical compositions comprising a compound of general formula (I), the use of the compound and of the pharmaceutical composition in the preparation of a medicament and in methods for the treatment or prevention of prothrombic states in disorders which are associated with excessive procoagulant activity, initiated or propagated by CMLA loss. The invention relates also to the use of the compound and of the pharmaceutical composition for the diagnosis of CMLA loss; as a targeting agent; as targeting drugs to tissues inflicted by CMLA loss; and for basic research in fields of research in which CMLA loss takes place both in vitro and in vivo.

47 Claims, 20 Drawing Sheets

U.S. PATENT DOCUMENTS

| | | | |
|---|---|---|---|
| 4,350,594 A | 9/1982 | Kawai et al. | 210/637 |
| 4,572,724 A | 2/1986 | Rosenberg et al. | 55/159 |
| 5,552,290 A | 9/1996 | Michelson et al. | 435/7.21 |
| 5,567,615 A | 10/1996 | Degen et al. | 435/280 |
| 5,608,060 A | 3/1997 | Axworthy et al. | 540/474 |
| 5,630,946 A | 5/1997 | Hart et al. | 210/805 |
| 5,630,996 A | 5/1997 | Reno et al. | 424/1.49 |
| 5,744,047 A | 4/1998 | Gsell et al. | 210/767 |
| 5,834,433 A | * 11/1998 | Krstenansky | 514/16 |

FOREIGN PATENT DOCUMENTS

| | | |
|---|---|---|
| WO | WO 91/04628 | 4/1991 |
| WO | WO 95/34315 | 12/1995 |
| WO | WO 96/29403 | 9/1996 |
| WO | WO 97/01760 | 1/1997 |
| WO | WO 97/35971 | 10/1997 |
| WO | WO97/40059 | 10/1997 |
| WO | 97/40070 | * 10/1997 |
| WO | WO 98/05777 | 2/1998 |

OTHER PUBLICATIONS

Sabolovic et al., "Membrane Modifications of Red Blood Cells in Alzheimer's Disease", Jul.1997, pp. 217–220, J. Gerontol. A Biol. Sci. Med. Sci., 52(4):B.

Moumaris et al., "Effect of Fatty Acid Treatment in Cerebral Malaria–Susceptible and Nonsusceptible Strains of Mice", Dec.1995, pp. 997–999, J. Parasitol, 81(6).

Miltenyi Biotec Inc., "MACS Apoptotic Cell Isolation Kit", , , 251 Auburn Ravine Rd., Suite 208, Auburn CA 95603, brochure (not dated).

Muchmore et al., "X–ray and NMR Structure of Human Bcl–X , an Inhibitor of Programmed Cell Death", May 23, 1996, pp. 335–341, Letters to Nature, vol. 381.

Specifications and Drawings for Application Ser. No. 09/200,715, Filed: Nov. 27, 1998, ., Inventors: Ilan Ziv et al.,.

Specifications and Drawings for Application Ser. No. 09/622,058, Filed: Aug. 24, 2000, ., Inventors: Ilan Ziv et al.,.

Specifications and Drawings for Application Ser. No. 09/511,378, Filed: Feb. 23, 2000, ., Inventors: Anat Shirvan et al.,.

Mercy Joseph et al., "Conformations of Peptides Corresponding to Fatty Acylation Sites in Proteins", pp. 19439–19440, Aug. 18, 1995, The Journal of Biological Chemistry, vol. 270, No. 33.

* cited by examiner

SEQUENCE LISTING

<160> NUMBER OF SEQ ID NOS: 3

<210> SEQ ID NO 1
<211> LENGTH: 29
<212> TYPE: PRT
<213> ORGANISM: Homo sapiens

-continued

```
<400> SEQUENCE: 1

Gly Gly Gly Lys Lys Lys Lys Lys Arg Phe Ser Phe Lys Lys Ser Phe
  1               5                  10                  15

Lys Leu Ser Gly Phe Ser Phe Lys Lys Asn Lys Lys Lys
            20                  25

<210> SEQ ID NO 2
<211> LENGTH: 26
<212> TYPE: PRT
<213> ORGANISM: Homo sapiens

<400> SEQUENCE: 2

Lys Lys Lys Lys Lys Arg Phe Ser Phe Lys Lys Ser Phe Lys Leu Ser
  1               5                  10                  15

Gly Phe Ser Phe Lys Lys Asn Lys Lys Lys
            20                  25

<210> SEQ ID NO 3
<211> LENGTH: 29
<212> TYPE: PRT
<213> ORGANISM: Homo sapiens

<400> SEQUENCE: 3

Gly Gly Gly Lys Lys Lys Lys Lys Arg Phe Ser Phe Lys Lys Ser Phe
  1               5                  10                  15

Lys Leu Ser Gly Phe Ser Phe Lys Lys Asn Lys Lys Lys
            20                  25
```

BASIC PEPTIDES AND PHARMACEUTICAL COMPOSITIONS CONTAINING SAME

The present invention relates to novel compounds and pharmaceutical preparations comprising same, their use in the treatment of and in the diagnosis of certain diseases, in particular of diseases involving changes of cell membrane lipid asymmetry (CMLA) is the phenomenon, by which normal eukaryotic cells have an asymmetrical organization of the phospholipids comprising their plasma membranes; the outer membrane leaflet is formed predominantly with the cholinephospholipids: (phosphatidylcholine [PC] and sphingomyelin), whereas the majority of the amino phospholipids (phosphatidylserine [PS] and phosphoethanolamine [PE]) are confined to the membrane's inner leaflet (Zwaal R F A & Schronit A J, Blood 1997;89:1121–1132) The physiolocical importance of CMLA is exemplified by the fact that its maintenance requires a continuous, considerable investment of energy by the cell (Seigneuret M & Devaux P F, Proc. Natl. Acd. Sci., 1984;81:3751) At least three distinct systems are active in the regulation of CMLA:

1. Aminophospholipid translocase (APT): an ATP-dependent enzyme which transports PS and PE from the outer to the inner membrane leaflet, against the concentration gradient (Daleke D L & Huestis W H, Biochemistry 1985;24:5406).

2. ATP-dependent floppase: transports aminophospholipids and cholinephospholipids from the inner to the outer leaflet. This enzyme is tenfold slower than APT (Andrick C et al., Biochim. Biophys. Acta 1991;1064:235).

3. Lipid scramblase: A potent, $Ca^{2+}$-dependent and ATP-independent enzyme, that rapidly moves phospholipids back and forth between the two membrane leaflets (flip-f-lo), leading within minutes to loss of CMLA (Zwaal R F A & Schronit A J, Blood 1997;29:1121–1132)

In addition, other factors, such as membrane anchoring of cytoskeletal proteins have been suggested to assist in CMLA maintenance.

Whereas the maintenance of CMLA is fundamental to normal cell physiology, its loss, with subsequent surface exposure of PS plays a role in numerous states of both physiological and pathological characters. The surface exposure of anionic phospholipids plays an indispensable role in the formation of a catalytic surface for the assembly of several clotting factor complexes. Thus, the loss of CMLA in activated platelets as well as in other cell types (e.g. endothelial cells), is an important factor in normal blood coagulation. However, CMLA loss also assists in the initiation and/or propagation of abnormal, excessive blood clotting in numerous disorders. These disorders include, among others:

1. Arterial or venous thrombosis (Thiagarajan P & Benedict C R, Circulation 1997;96:2339–2347; Van Ryn McKenna J, et al., Throm. Hemost. 1993;69:227–230).

2. Sickle cell disease (Tait J F & Gibson D, J. Lab. Clin. Med. 1994;123:741).

3. Beta-thalassemia (Borenstein-Ben-Yashar Y, et al., Am. J. Hematol. 1994;47:295; Ruf A, et al., Br. J. Haematol. 1997;98:51–56).

4. Antiphospholipid antibody syndrome; among others in systemic lupus erythematosus. Lack of CMLA has been specifically linked to the recurrent abortions associated with said syndrome (Rand J H, et al., N. Engl. J. Med. 1997;337:154–160).

5. Shed membrane microparticles, e.g., during cardiopulmonary bypass, (Nieuwland R et al., Circulation 1997;96:3534–3541; Aupeix K, et al., J. Clin. invest. 1997; 99:1546–155).

Apoptosis is another major situation in which CMLA loss takes place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters or membrane-bound particles (apoptotic bodies), which are thereafter engulfed by macrophages (Boobis A R, et al., Trends Pharmacol. Sci. 10:275–280, 1989; Bursch W, et al., Trends Pharmacol. Sci. 13:245–251, 1992). Loss of CMLA is quite a universal phenomenon in apoptosis (Van den Eljnde S M, et al., Cell death Diff. 1997;4:311–316). Loss of CMLA occurs early in the apoptotic cascade, immediately following the point of cell commitment of the death process (Van-Engeland M, et al., Cytometry 1998;31:1–9; Martin S J, et al., J. Exp. Med. 1995;182:1545–1556). It has also been shown that the loss of CMLA is an important factor in the recognition and removal of apoptotic cells by macrophages (Balasubramanian K, et al., J. Biol. Chem. 1997;272:31113–31117). A strong correlation has recently been drawn between the loss of CMLA and the potent pro-coagulant activity of apoptotic cells (Bombeli T, et al., Blood 1997; 89:2429–2442; Flynn P D, et al., Blood 1997;89:4378–4384) The latter activity in apoptotic endothelial cells, such as those recently recognized in atherosclerotic plaques (Kockx M M, et al., Circulation 1998;97:2307–2315, Mallat Z, et al., Circulation 1997;96:424–428), probably plays an important role in the pathogenesis of thrombotic vascular disorders.

The diagnosis of the loss of CMLA may therefore serve as an important tool for the detection of cell death, specifically by apoptosis. A method for the detection of cell death may have many applications, both as a diagnostic tool and as a method to monitor the disease course in numerous disorders associated with impairment of tissue homeostasis. Among these applications are:

1. Monitoring of a response to anti-cancer therapy:

Currently there is a lag period between the time of administration of anticancer drugs and the time of evaluation or their efficacy. Thus, in case of failure of a therapeutic regimen, this lag time may be hazardous to the patient in two aspects:

a. loss of precious time without an effective therapy; and b. unnecessary exposure of the patient to drug adverse effects.

Therefore, there is clearly a need for an early detection of tumor response to treatment. Since anti-tumor drugs exert their effects by induction of apoptosis (Eastman A, Cancer Cells, 1990;2:275–280), the detection of apoptosis, potentially by detection of CMLA loss may be useful for monitoring tumor response.

2. Diagnosis of disorders of inappropriate excessive apoptosis. These disorders include, among others, AIDS, neurodegenerative disorders, myelodysplastic syndromes and various ischemic or toxic insults (Thompson C B, Science 1995;267:1456–1461).

3. Monitoring of graft survival following organ transplantation. The increasing use of organ transplantation for the treatment of end-stage organ failure emphasizes the need for the development of methods for sensitive monitoring of graft survival. Apoptosis plays a major role in graft cell loss (Matsuno T, et al. Transplant Proc. 1996;28;1226–1227; Dong C et al., Lab. Invest. 1996;74:921–931).

4. Monitoring of response to cytoprotective treatments. The current intensive research of cytoprotective agents, towards development of drugs capable or inhibiting cell loss in various diseases (Thompson C B, Science 1995;267:1456–1461), dictates a need for measures to evaluate the effects of such compounds, i.e., monitoring of cell death, in all levels of research, from in vitro tissue culture studies, through in vivo animal models to human clinical studies.

5. Basic research of apoptosis in tissue cultures and animal models.

The loss of the normal CMLA has, as indicated above, wide implications for various pathophysiological states. A compound capable of selectively binding to membranes upon CMLA loss, thus serving as a marker for this phenomenon, may therefore have wide diagnostic applications. Moreover, by shielding the exposed anionic phospholipids, specifically PS, such compound may be a useful therapeutic agent, for example for the above-mentioned disorders, which are associated with excessive pro-coagulant activity caused by the membrane phospholipid re-organization.

In addition, a compound capable of detecting cells undergoing apotosis may have important applications for targeting drugs to apotosis-inflicted tissues. Apoptosis and its major control systems are shared by all tissues in the body. Therefore, the implementation of the emerging new generation or drugs, active by modulation of apotosis control is expected to depend, at least in part, on the ability to target these drugs to the appropriate tissues. An apoptosis-detecting compound may thus be useful for this task.

There have been developed certain measures for the effective detection of cell death in tissue cultures, such as the TUNEL (terminal deoxynucleotidyl transferase-mediated dUTP-biotin end-labeling) method, for the detection of the characteristic chromatin cleavage of apoptotic cells. However, this method, as well as other methods such as the DNA laddering method, are strictly limited to the in vitro level.

The potential of a detector of CMLA loss both as a diagnostic tool and as a therapeutic measure has recently been exemplified by the use of annexin-V for these indications. Annexin V is a member of the annexin family of proteins, sharing potent, $Ca^{2+}$-dependent binding to anionic phospholipid membranes (Swairjo M A, et al., Nature Struc. Biol. 1995;968–974). Annexin V is a 320 amino acid protein, with a molecular mass of 35,935 daltons (Huber R, et al., EMBO J. 1990;9:3867–3874) Though the physiological role of annexin-V has not been fully elucidated, it has been suggested to be involved in anticoagulation, anti-inflammation and cellular signaling (Romisch J, et al., Thromb. Res. 1990;60:355–366; Bastian B C, J. Invest Dermatol. 1993; 101:359–363; Kaneko N, et al., J. mol. Biol. 1997;274:16–20). The impressive affinity of annexin V to anionic phospholipid membranes (Kd of about $10^{-9}$–$10^{-11}$M, [Hofmann A, et al., Biochim. Biophys. Acta, 1997;254–264]) has been extensively utilized for both the diagnosis of CMLA loss and modulation of disorders associated with this phenomenon. Fluorescein isothiocyanate (FITC)-labeled annexin V has been widely used for the detection of apoptosis in various tissue culture models (Koopman G, et al., Blood 1994;84:1415–1420; Rimon G, et al., J Neurosci Res 1997; 48:563–570; Van-Engeland M, et al., Cytometry 1998;31:1–8). Preliminary successful studies were also performed with systemic intracardial injection of biotinylated annexin v to viable mouse embryos, for the detection of developmentally-associated apoptosis (Van den Eijnde S M, et al., Cell death Diff. 1997;311–316). Systemic administration of $^{99m}$Tc-annexin V was also used to detect and image cell death in several models in vivo, e g. fulminant hepatitis in mice, acute rejection of transplanted cardiac allograft in rats and monitoring of response of lymphoma to cyclophosphamide treatment in mice (Blankenberg F G. et. al. Proc. Natl. Acad. Sci. USA, 95:6349–6354, 998). $^{125}$I-labeled annexin V was also used for in vivo detection of thrombosis in an animal model (Stratton J R, et al., Circulation 1995;92:3113–3121). Inhibition of arterial thrombosis was effectively achieved by intravenous administration of annexin V in a carotid artery injury model (Thiagarajan P & Benedict C R, Circulation 1997;906:2339–2347). Annexin V is also known as diagnostic agent (U.S. Pat. No. 5,627,036).

However, the use of annexin V as a drug or as a diagnostic probe is rendered problematic by several characteristics of this protein. Annexin V is a protein of considerable size, a factor which may substantially limit its volume of distribution in the body. Moreover, it is active as a potent membrane-binding protein only if allowed to form a highly organized multimer on the membrane surface (Concha NO, et al., FEBS Lett 1992;314:159–162; Voges D, et al., J. Mol. Biol. 1994;238:199–213, Andree H A M, et a., J. Biol. Chem 1992;26:17907–17912). Thus, systemic administration of annexin V as a drug is expected to be associated with rapid degradation and loss of the function of the administered protein. Indeed, a very rapid clearance (90% within 5 minutes) was observed in rabbits following intravenous injection of annexin V (Thiagarajan P & Benedict C R, Circulation 1997;96:2339–2347). In addition, the administration of annexin V may induce an untoward immunological response, importantly, anti-annexin V antibodies have been recently implicated in the pathogenesis of anti-phospholipid antibody syndrome and associated thrombotic events (Nakamura N, et al., Am. J. Hematol. 1995; 49:347–348; Kaburaki J & Ikeda Y, Rinsho Ketsueki 1995;36:320–324, Rand J H, et al., N. Engl. J. Med. 1997;337:154–160).

There exists therefore a need for novel methods for the detection of cell death, specifically at the in vivo level. A method for the detection or loss of CMLA may be useful for this purpose.

Moreover, it is also desirable to develop novel compounds, for the diagnosis of CMLA loss, the modulation of its pathophysiological consequences and for the treatment of certain diseases in which said CMLA loss plays a role.

The present invention thus consists in a compound (hereinafter: "NST300 compound") of general formula I comprising the following components:

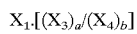

wherein:
- $X_1$ stands for a saturated or unsaturated fatty acid residue comprising 6–20 carbon atoms; or a cysteine residue bound through a thioether bond to a prenyl group comprising 5–20 carbon atoms, said residue being linked to the adjacent component of the compound through an amide bond;
- $X_3$, comprises 1–6 amino acids, of which 1–6 are positively charged, the other amino acid residues being polar uncharged amino acids; and
- $X_4$ comprises 1–6 amino acids, of which 1–2 are aromatic amino acids, the other amino acids being selected among polar uncharged amino acids and hydrophobic aliphatic amino acids;

wherein:
a stands for an integer of 1–8; and
b stands for an integer of 1–8;
the groups $X_3$ and $X_4$ being located at various places in the compound.

For the sake of clarity it should be indicated that the term "prenyl" herein, stands also for the term "isoprenyl" (see Stedman's Medical Dictionary, Baltimore, USA, William and Wilkins, eds., 1990:565, 1253).

$X_1$ serves as main anchoring domain A;:
$X_3$ serves as anionic phospholipid binding determinant; and
$X_4$ serves as accessory anchoring domain.
$X_0$ is advantageously a residue of a saturated fatty acid of formula $CH_3(CH_2)_nCO_2H$, in which n stands for an integer of 8–18 preferably selected among myristic acid and palmitic acid; or $X_1$ is advantageously a cysteine-residue bound through a thioether bond to a prenyl of 5–15 carbon atoms, preferably farnesyl cysteine.

The positively charged amino acids of $X_3$ are advantageously selected among lysine, arginine, histidine or any amino acid which is comprised of a positively charged group, e.g. primary amine, secondary amine, guanidine, covalently bound to the α-carbon atom or to the α-amine on the peptide backbone bad a spacer comprised of an alkene of 1–4 carbon atoms; and combinations thereof; the other amino acids that are not positively charged are polar uncharged. The acids are preferably selected among lysine and arginine and combinations thereof. The polar uncharged amino acids of $X_3$ are preferably selected among serine, threonine, asparagine and glutamine and combinations thereof.

The aromatic amino acids of $X_4$ are preferably selected among phenylalanine and tryptophan and combinations thereof; the polar uncharged amino acids are preferably selected among serine, asparagine and glutamine and combinations thereof; and the hydrophobic aliphatic amino acids are preferably selected among leucine, alanine and glycine and combinations thereon.

The compound according to the present invention may comprise additional groups $X_2$, $X_5$ and $X_6$ in which case it has general formula Ia

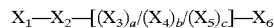

wherein: $X_1$, $X_3$ and $X_4$ have the same meaning as above,
$X_2$ is selected among 0–3 glycine residues and 0–2 β-amino alanine molecules;
$X_5$ is a compound of general formula II

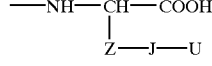

wherein Z stands for a spacer group selected among alkane and alkene containing 1–5 carbon atoms, J stands for a functional group selected among amines, thiols, alcohols, carboxylic acids and esters, aldehydes and alkyl halides; U is a labeling group c standing for an integer of 0–10; and
$X_6$ being 0; or being selected among $X_1$ (as hereinbefore defined);
within the subunit $[(X_3)_a/(X_4)_b/(X_5)_c]$ the groups $X_3$, $X_4$ and $X_6$ may be located at various suitable places.
$X_2$ serves as linker A, between $X_2$ and the sub-unit $[(X_3)_a/(X_4)_b]$ or between $X_2$ and the sub-unit $[(X_3)_a/(X_4)_b/(X_5)_c]$;
$X_5$ serves as linker B between the sub-unit $[(X_3)_a/(X_4)_b]$ and $X_6$ or between the sub-unit $[(X_3)_a/(X_4)_b/(X_5)_c]$ and $X_6$; and
$X_6$ serves as main anchoring domain B.

U as a labeling group for specific binding is advantageously selected among biotin and a group containing a substituent selected among a fluorescein, a radioisotope and a paramagnetic contrast agent; the fluorescein may be, for example, fluorescein isothiocyanate; the radioisotope may be selected among technetium, lead, mercury, thallium and indium; and the paramagnetic contrast agent may be any paramagnetic metal ion chelate, e.g. gadolinium-diethylenetriaminepentaacetic acid (Gd-DTPA).

$X_5$ is advantageously a lysine residue substituted at the α-amino group by a labeling group as above defined.

In case that $X_6$ stands for a cysteine residue bound through a thioether bond to a prenyl group the cysteine carboxyl group can be either free or methylated.

Any of the above amino acids may be the L-, the D- or the DL isomer or the racemate.

The amino acid residues may also be residues of suitable synthetic amino acids.

A sequence of the compounds of general formulae I and Ia is:
Myristate-
GGGKKKKKRFSFKKSFKLSGFSFKKNKKK (SEQUENCE ID NO. 1)-U, in which G=glycine, K=lysine, R=arginine, F=phenylalanine, S=serine, L=leucine, N=asparagine and U as hereinbefore defined.

A preferred compound of said sequence is:
Myristate-
GGGKKKKKRFSFKKSFKLSGFSFKKNKKK (SEQUENCE ID NO. 1)-(biotin). (This compound is herein called "NST301".)

Another sequence of the compounds of general formulae I and Ia is
Myristate-KKKKKRFSFKKSFKLSGFSFKKNKKK (SEQUENCE ID NO. 2)-U, wherein K, R, F, S, L, G, N and U have the same meaning as above.

A preferred compound of said sequence is:
Myristate-KKKKKRFSFKKSFKLSGFSFKKNKKK (SEQUENCE ID NO. 2)-(biotin). (This compound is herein called "NST302".)

The present invention also consists in pharmaceutical compositions comprising as active ingredient a NST300 compound as defined above with reference to genera formulae I and Ia. (Whenever the NST300 compound is mentioned herein it refers to the appropriate compounds as defined in formulae I and Ia).

In a preferred embodiment the pharmaceutical composition comprises in addition to the NST1300 compound a pharmaceutically acceptable carrier.

The carriers may be selected among any suitable components, e.g. solvents; emulgators; excipients; talc; flavors; colors; etc. The pharmaceutical composition may comprise, if desired, also other pharmaceutically active compounds. The pharmaceutical compositions may be, e.g. tablets, capsules, solutions, emulsions, etc.

The pharmaceutical composition according to the present invention may comprise an additional pharmaceutically active compound.

The amount of the NST300 compound incorporated in the pharmaceutical composition may vary widely. The factors which have to be considered when determining the precise amount are known to those skilled in the art. Such factors include, inter aria, the pharmaceutical carrier being part of the composition, the route of administration being employed and the frequency with which the composition is to be administered.

The pharmaceutical composition may be administered by any of the known methods, inter alia, per os, intravenous, intrapertional, intramuscular or subcutaneous or topical administration.

The present invention further consists in the use of a NST300 compound or of a pharmaceutical composition comprising same in the preparation of a medicament, in particular for the treatment or prevention or prothrombotic states; advantageously for the treatment of disorders which are associated with excessive pro-coagulant activity, initiated or propagated by CMLA loss, such as arterial or venous thrombosis; sickle cell disease; thalassemia; antiphospholipid antibody syndrome; lupus erythematosus; shed membrane particles, (e.g. during cardiopulmonary bypass); apoptosis, etc.

The present invention also consists in a method for the treatment or prevention of prothrombotic states; advantageously for the treatment of disorders which are associated with excessive pro-coagulant activity, initiated or propagated by CMLA loss, such as arterial or venous thrombosis; sickle cell disease; thalassemia; antiphospholipid antibody syndrome; lupus erythematosus; shed membrane particles, (e.g. during cardiopulmonary bypass); apoptosis, etc. by a NST300 compound or by a pharmaceutical composition comprising same.

The present invention also consists in the use of a NST300 compound or of a pharmaceutical composition comprising same for the diagnosis of CMLA loss. Said use may be performed either in vitro or in vivo in accordance with the specific requirements. Said uses are especially:
 a. use as a diagnostic agent for the detection and imaging of cell death, particularly of apoptosis, either in vitro or in vivo. The in vitro imaging is preferably performed with fluorescin; the in vivo imaging is preferably performed by a scan with an isotope or by MRI;
 b. use as a diagnostic agent for thrombosis or for prothrombotic states; and
 c. use as a diagnostic agent for pathophysiological states associated with apoptosis; e.g monitoring of response to anticancer treatments, diagnosis of disorders of inappropriate excessive apoptosis, monitoring of response to cytoprotective treatments, monitoring of graft survival following organ transplantation.

The present invention also consists in a diagnostic kit comprising a NST300 compound or a pharmaceutical comprising same for the performance of the diagnostic steps.

The present invention also consists in the use of a NST300 compound or of a pharmaceutical composition comprising same as a targeting agent, to target drugs to tissues inflicted by CMLA loss, preferably tissues the cells of which are inflicted by excessive apoptosis, or tissues in which thrombosis in association with CMLA loss takes place.

The present invention also consists in a method for targeting drugs to tissues in the body which are inflicted by CMLA loss, which method comprises the conjugation of a NST300 compound or a pharmaceutical composition comprising same with a drug to be targeted through an esteric bond. The NST300 compound directs the conjugate to regions of CMLA loss. Subsequently, naturally-occurring cleavage or the esteric bond by local tissue esterases allows the liberation of the targeted drug to act in said region. The tissues are in particular those tissues the cells of which are inflicted by excessive apoptosis or tissues in which thrombosis in association with CMLA loss takes place.

The present invention also consists in the use of NST300 compounds or of pharmaceutical compositions comprising same for basic research, in fields of research in which CMLA loss takes place, both in vitro and in vivo, inter alia, of cell cultures, preferably in basic research of apoptosis.

Moreover, the present invention further consists in a process for the preparation of a NST300 compound of general formula I by the following steps:
 a. for the preparation of the sub unit $[(X_3)_a/(X_4)_b]$ an α-amine protected, c-terminal amino acid of said sequence is loaded on a solid support, the α-amine protecting group is removed, and the peptide sequence is sequentially prepared;
 b. for coupling to $X_1$ the α-amino protecting group is removed from the N-terminal amino acid, and $X_1$ is then introduced into the peptide-resin under the same conditions as in step a; and
 c. finally the peptide is cleaved from the solid support, purified and characterized.

NST300 compounds of general formula Ia comprising sub-unit $[(X_3)_a/(X_4)_b/(X_5)_c)]$ are prepared according to step (a) above.

For the preparation of $X_5$ and its coupling to a labeling group or to $X_6$ an orthogonally protected amino acid is loaded on a solid support; the protecting group on the ω-functional group is selectively removed; $X_6$ or the labeling group of $X_5$ is introduced into the amino acid-resin in the Presence of an appropriate coupling reagent or by using a pre-activation method.

The coupling agent may be HBTU/HOBT and the pre-activation method may be the formation of an ester, azide or an anhydride.

Step (a) may also be used for the integration of $X_5$ (either coupled to a labeling group or coupled to $X_6$) into the peptide sequence.

The characterization is preferably performed by high performance liquid chromatography—mass spectra (HPLC-MS)

Step (a) and the pre-activating may be performed on the basis of knowledge of solid phase peptide synthesis (Atherton E, Sheppard R C, Solid phase peptide synthesis; a practical approach, IRL Press, 1989; Bodanszky M, Peptide Chemistry, Springer Verlag, 1988.)

The present invention will now be illustrated with reference to the following accompanying Figures and the Examples without being limited by same. In order to further clarify the performance of NST300 compounds, the performance of a control compound designated NST301-C is described for comparison in several of the Examples and Figures. The formula of NST301-C is:
 GGGKKKKKRFSFKKSFKLSGFSFKKNKKK (SEQUENCE ID NO. 3) (Biotin)-OH.

BRIEF DESCRIPTION OF THE FIGURES

FIG. 1: Structure of NST300 compounds:

FIG. 2: Binding of NST301 compound (750 nM) to single apoptotic cells: morphological studies.

FIG. 3. Detection of apoptotic cells by NST300 compounds; flow cytometric (FACS) analysis.

FIG. 5 NST300 compounds (500 nM) potently correct the pro-coagulant effect of apoptotic cells.

FIG. 6: NST302 inhibits binding of derived from SLE (Systemic Lupus Erythematasus) patients (lupus plasma) to anionic phospholipids.

DETAILED EXPLANATION OF THE FIGURES

FIG. 1: Structure of NST300 compounds
See text for detailed description of the composition of each domain. PS=phosphatidylserine, the main anionic phopholipid exposed on cell surface upon CMLA loss.

Figure 1A:
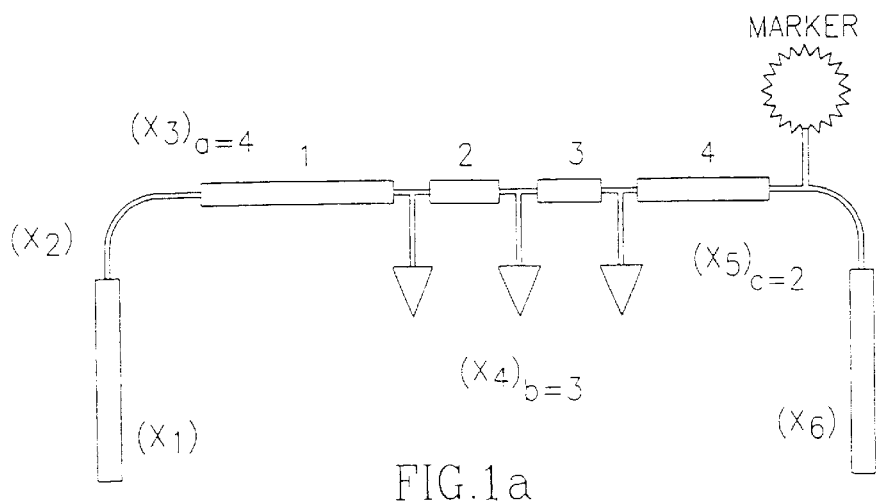
FIG. 1a: Example of main structural domains of NST 300 compounds (general formula Ia).

FIG. 1a: Example of main structural domains of NST 300 compounds (general formula Ia).

Figure 1B:
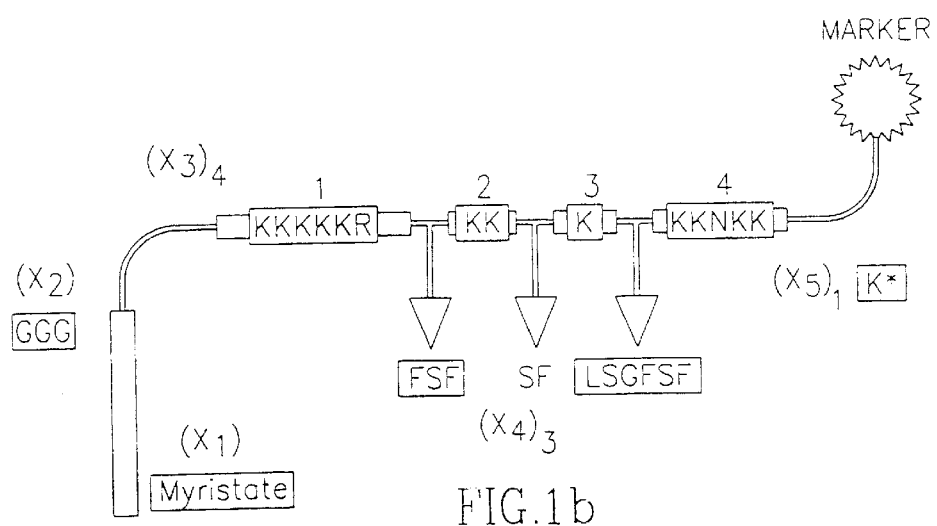
FIG. 1b: NST301 compound; detailed structure.

FIG. 1b: NST301 compound; detailed structure.

Figure 1C:
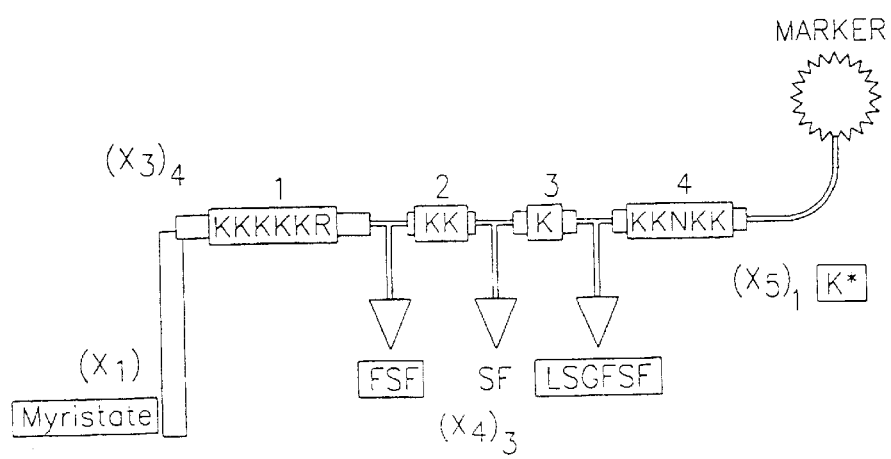
FIG. 1c: NST302 compound; detailed structure.

FIG. 1c: NST302 compound; detailed structure.

FIG. 2: Binding of NST301 compound (750 nM) to single apoptotic cells: morphological studies.

Figure 2A:
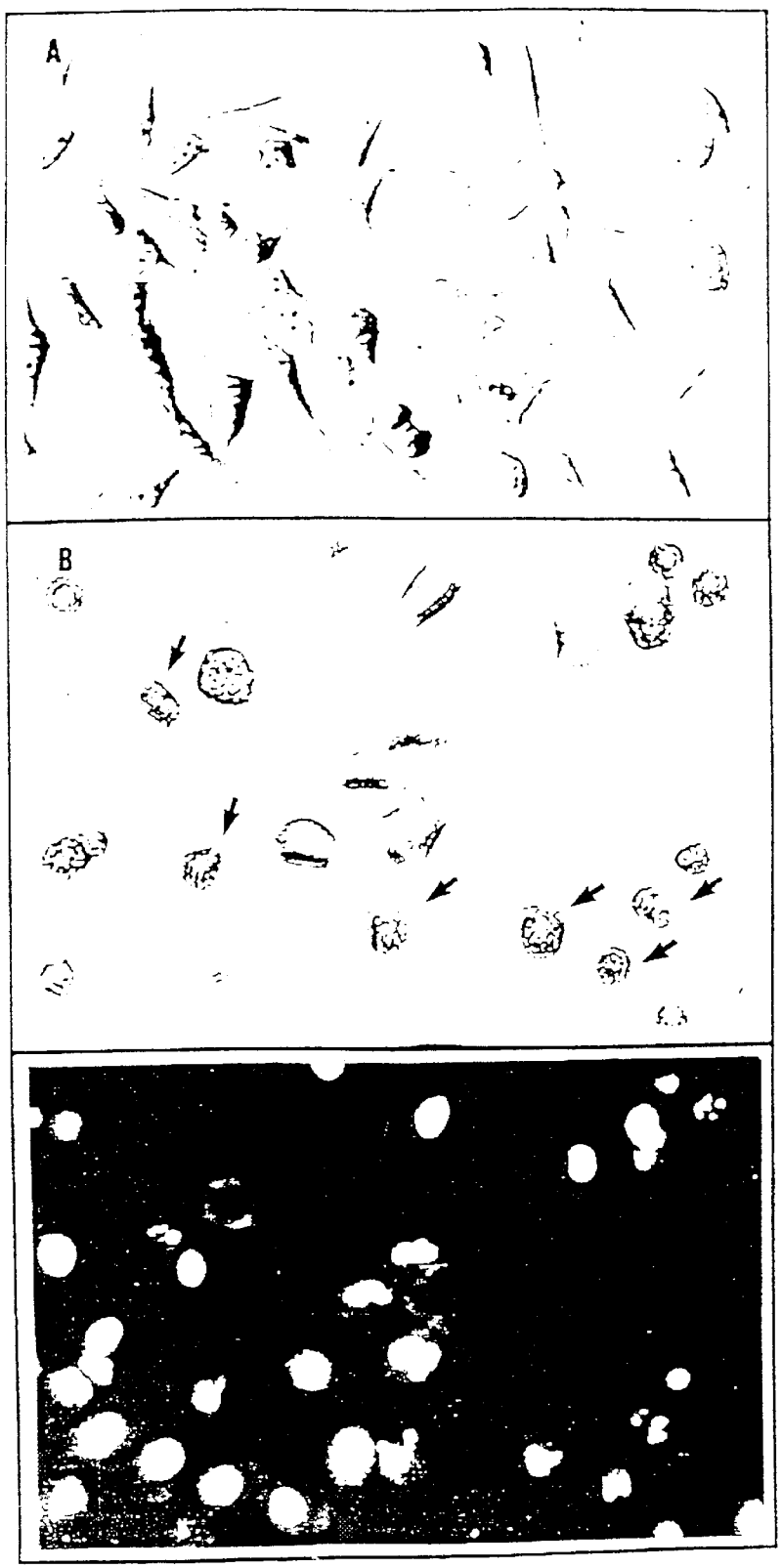
FIG. 2a: Cultured HeLa cells undergoing dopamine (DA)-induced apoptosis.

FIG. 2a: Cultured HeLa cells undergoing dopamine (DA)-induced apoptosis

HeLa cells grown on slides were induced to undergo apoptosis by 500 µM of DA for 18 hours, after which apoptotic cells were identified by Hoechst 33342 staining.
(A) Control, non-treated cells.
(B) DA-induced apoptosis in HeLa cells. Some of the apoptotic cells are indicated by arrows. As the result of the apoptotic trigger, very few cells are still attached to the glass slide.
(C) DA-induced apoptotic HeLa cells after staining with Hoechst 33342. The same field as in (B) is presented, and arrows point to the same apoptotic cells as in (B). 50% of the cells treated according to the above protocol were identified as apoptotic cells. Magnification X270.

Figure 2B:
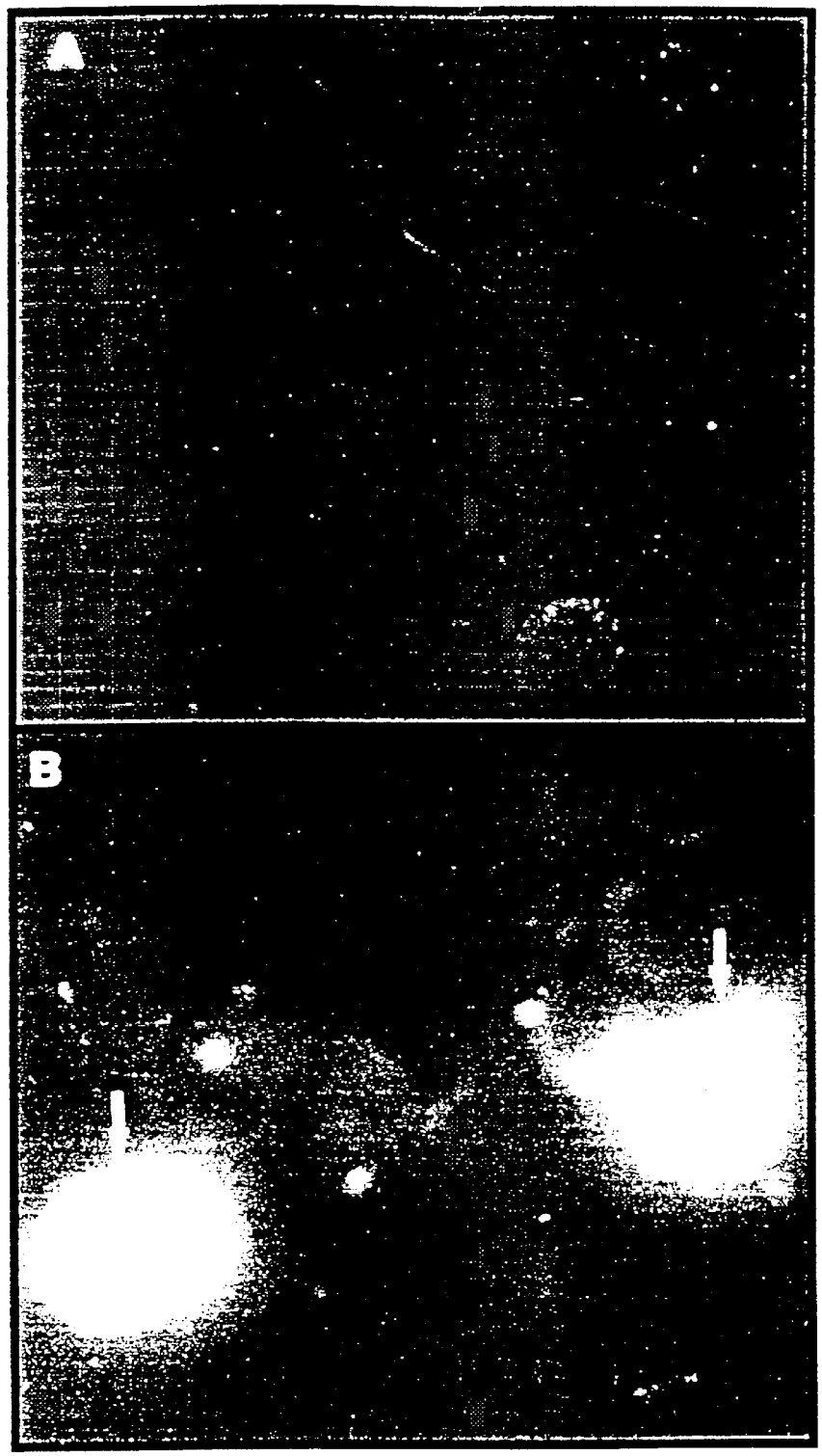
FIG. 2b: Detection of apoptosis by NST301 compound.

FIG. 2b: Detection of apoptosis by NST301 compound
Control HeLa cells (A) and dopamine (DA)-treated cells (B) were stained by 750 nM of NST301 and visualized by fluorescent microscopy. Although many healthy cells are present in this field (A) similarly to the field presented in FIG. 2A, few of them were stained, and very faintly with NST301. Apoptotic cells were stained by NST301, and typical cells are presented and marked by arrows in (B). Magnification X460.

Figure 2C:
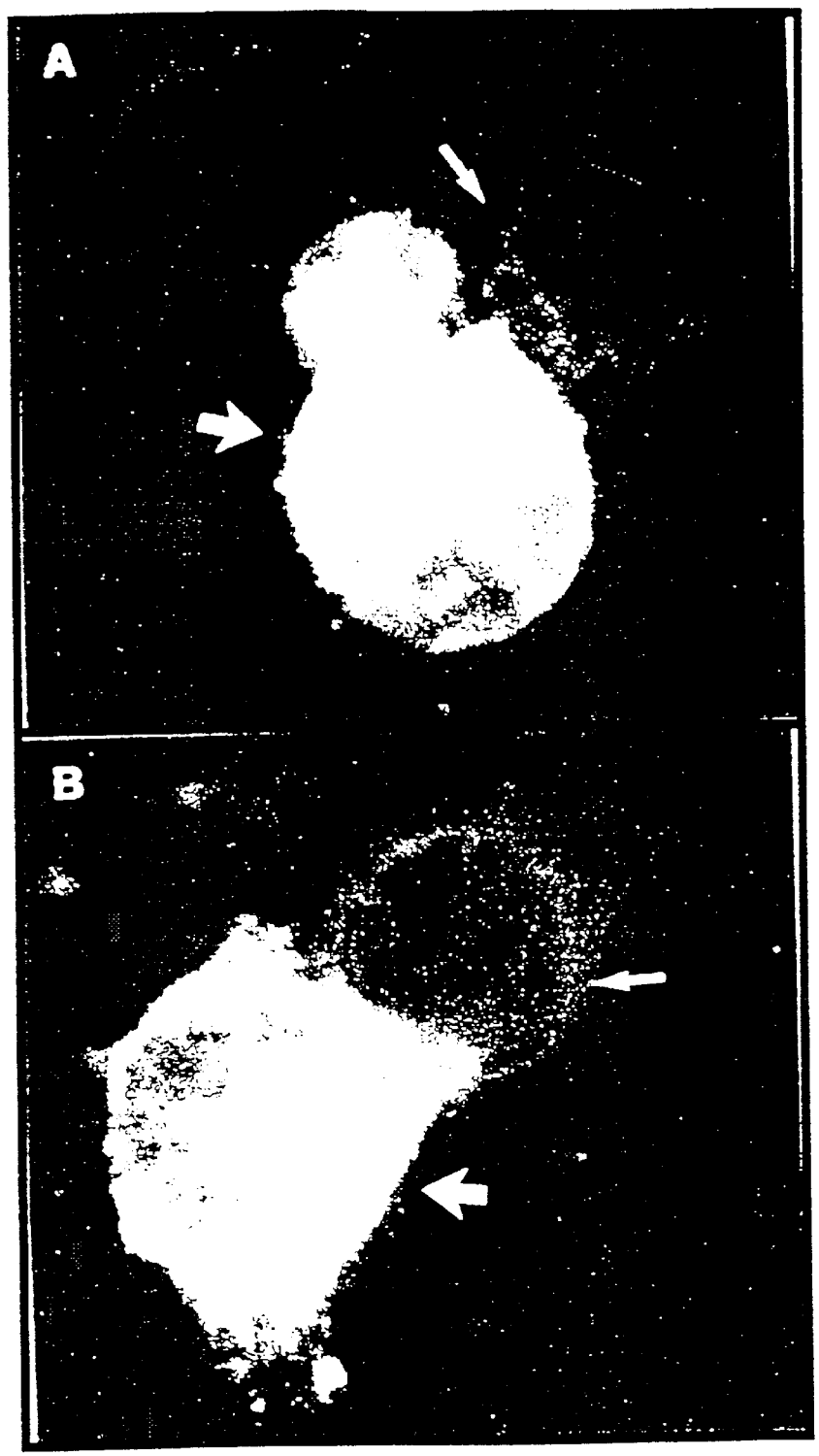
FIG. 2c: Detection of Apoptotic cells by NST301 compound.

FIG. 2c: Detection of Apoptotic cells by NST301 compound
Staining by NST 301 compound of cells undergoing various stages of apoptosis. Early apoptotic stages (light, peripheral staining) versus advanced apoptotic cells (intense labeling) Magnification X1200.

FIG. 3 Detection of apoptotic cells by NST300 compounds; flow cytometric (FACS) analysis.

Figure 3A:
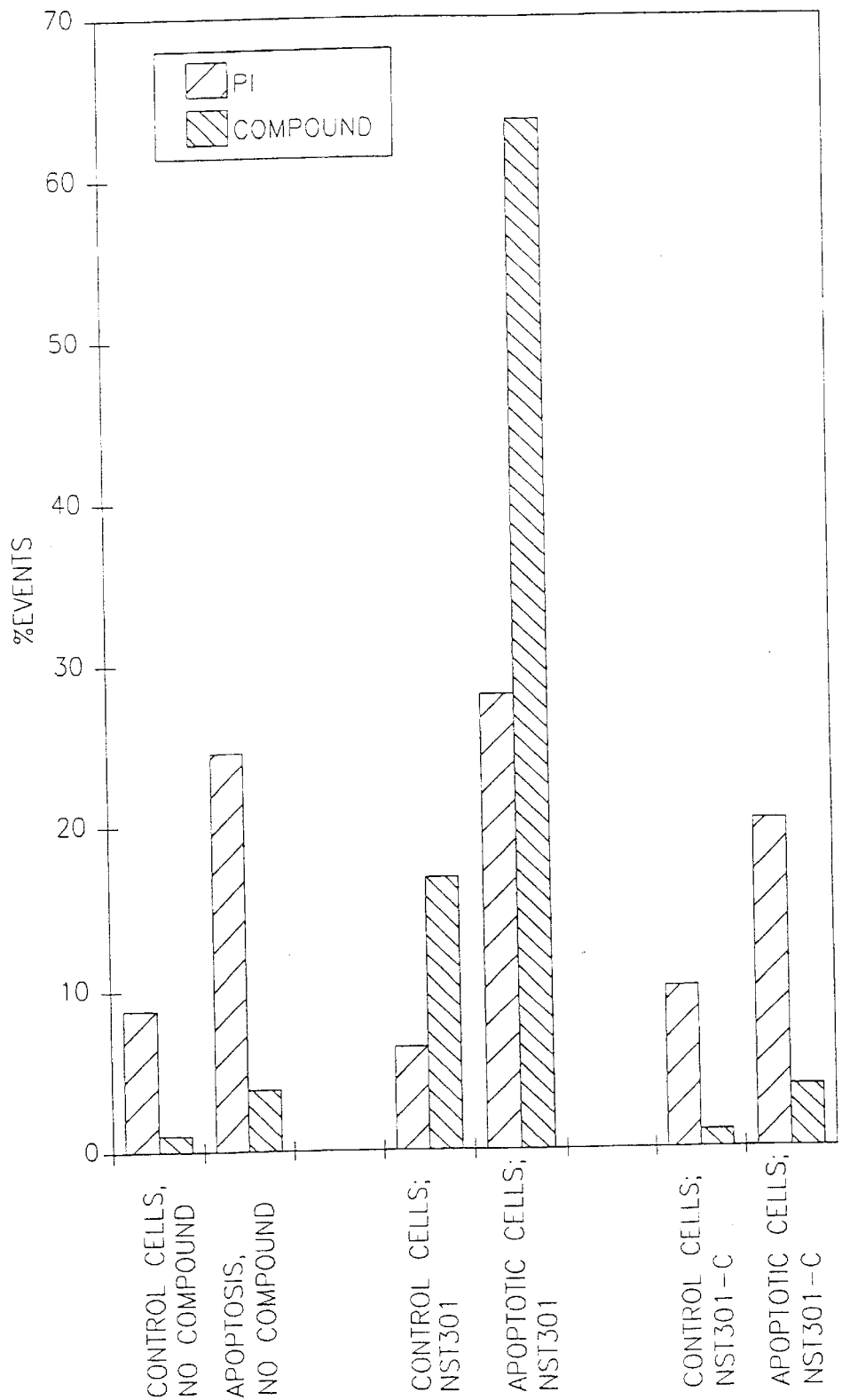
FIG. 3a: NST301 (750 nM) as a potent marker of apoptotic cells.

FIG. 3a: Binding of NST300 compounds to cells undergoing apoptosis: FACS analysis.
Three different types of cell populations (control, early and advanced apoptotis cells) were subjected to 3 different staining protocols:
(1) PI and FITC only with no compound.
(2) double staining with PI and NST301.
(3) double staining with PI and NST301-C.
For each of the treatments, the percentage of cells that were stained with FITC (indicative of binding of NST301 compound) and cells that were stained with PI, (indicative of loss of plasma membrane integrity, typical of advanced apoptotic stages) were determined. NST300 Compounds used for staining were at a concentration of 750 nM. As shown, NST301, but not the control compound NST301-C was a potent marker of the apoptotic cells.

Figure 3B:
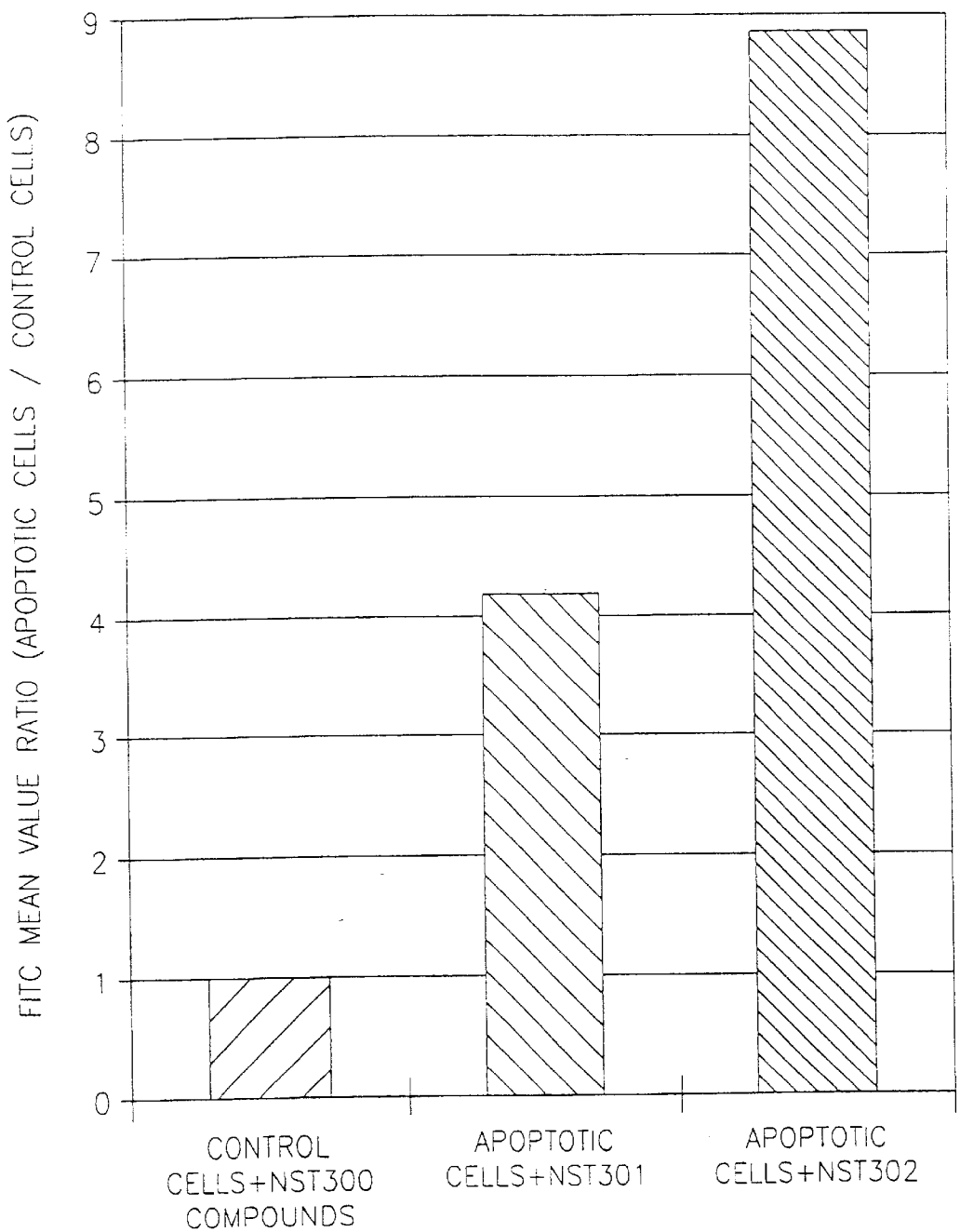
FIG. 3b: Relative binding intensity of NST300 compounds (750 nM) to apoptotic cells.

FIG. 3b: Binding intensity of different NST300 compounds to apoptoic cells
Control non-treated cells and early apoptotic cells were stained with 750nM of the different NST300 compounds. Binding intensity was defined as the ratio between FITC mean value of apoptotic cells to that of control cells.
NST301 compound showed a 4 fold increase in FITC intensity as compared to control. NST302 snowed a 9 fold increase in binding intensity.

Figure 3C:
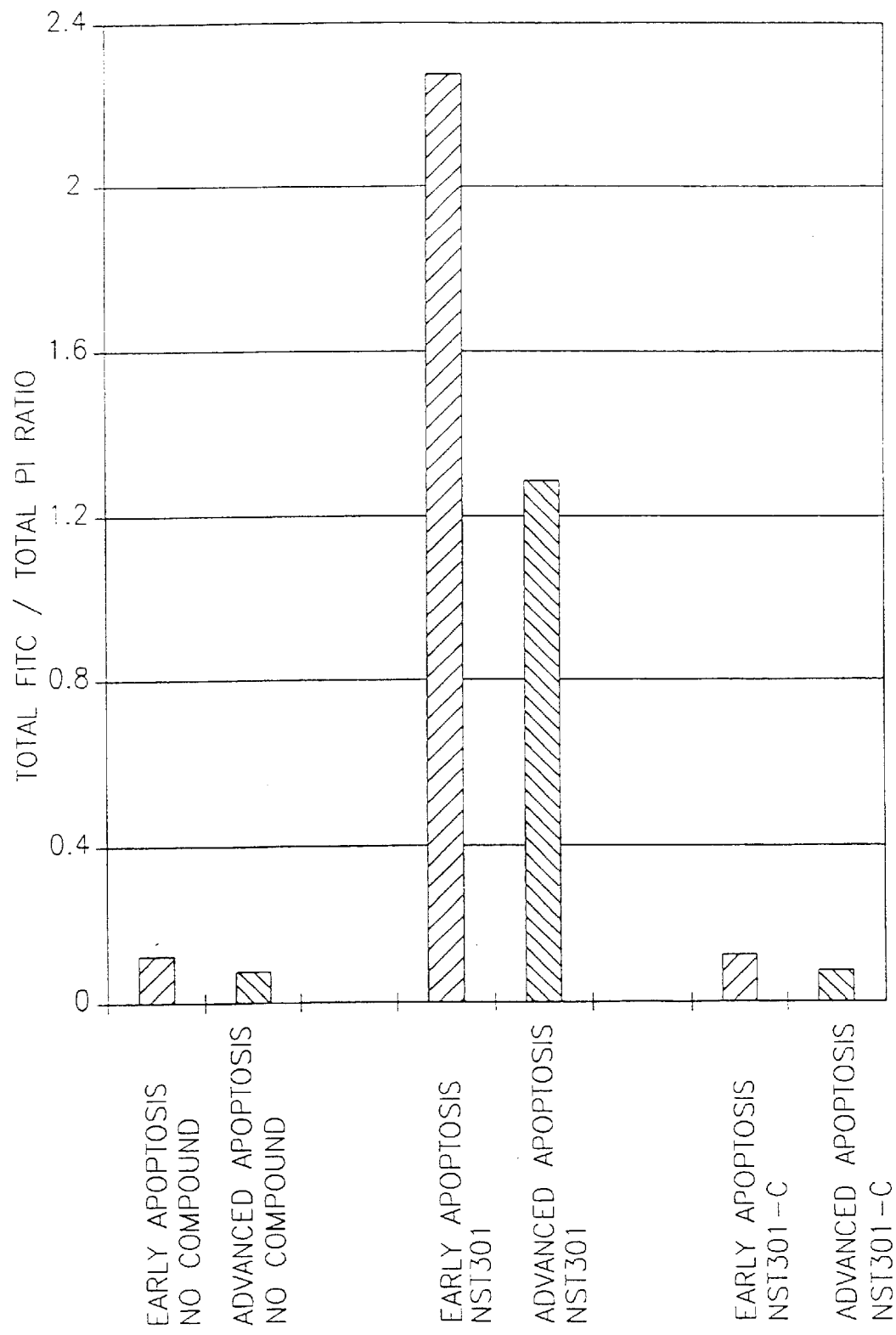
FIG. 3c: Detection of early apoptotis by NST301 compound (750 nM); total FITC/total PI ratio.

FIG. 3c: Detection of early apoptotic cell populations by NST300 compounds
The percentage of HeLa cells stained with FITC versus cells stained with PI was defined as an indicator of early apoptotic cell populations. These cells are characterized by loss of CMLA, while still retaining plasma membrane integrity. Before Staining with FITC and PI, early and advanced apoptotic cells were exposed to either one of the followings:
No treatment
Treatment with NST301, and
Treatment with NST301-C.
As shown, NST301 compound was a potent detector of the early apoptotic cells.

Figure 3D:
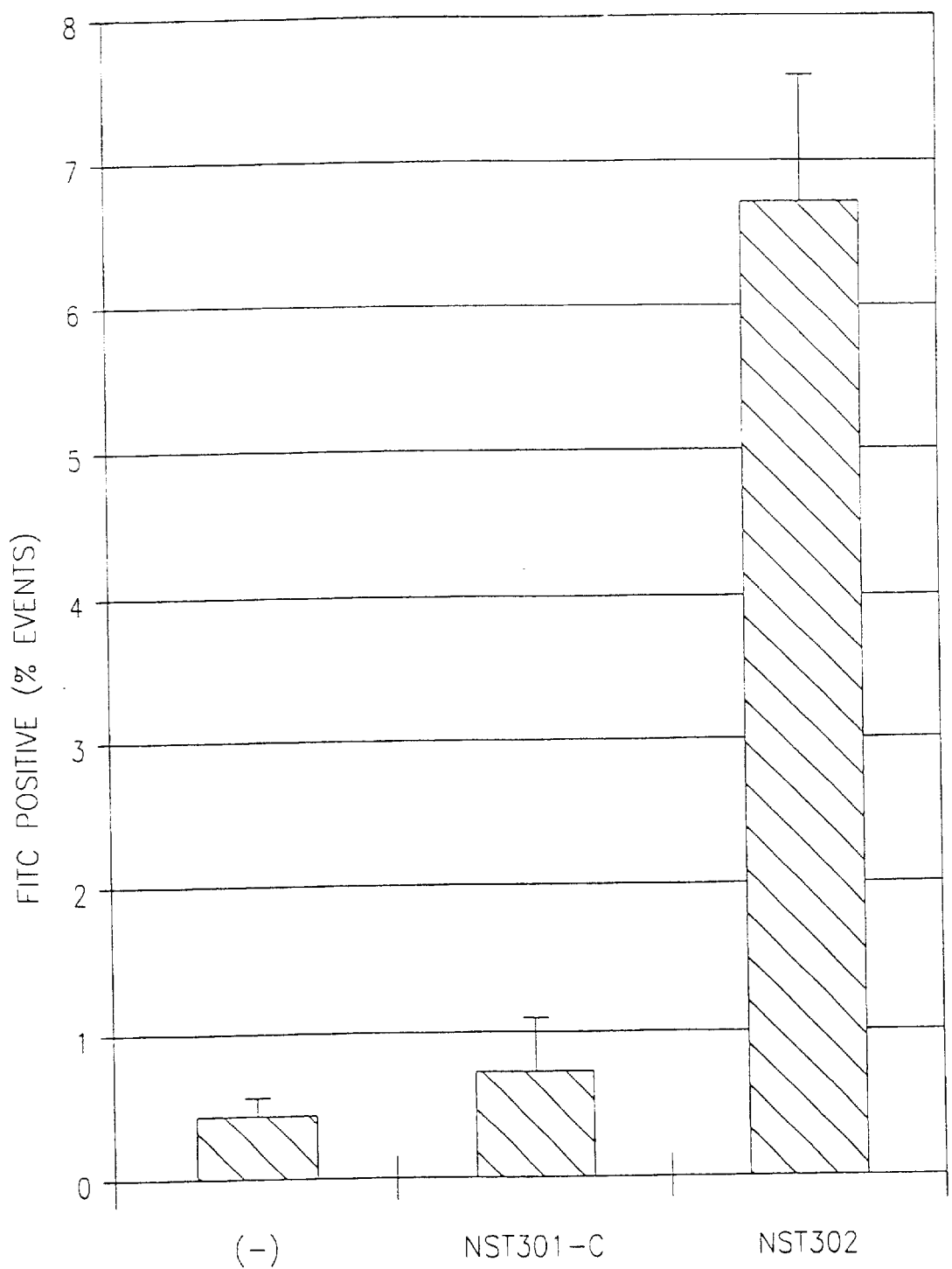
FIG. 3d: Binding of NST303 compound to Human umbilical cord endothelial cells (HUVEC).

FIG. 3d: Binding of NST303 compound to Human umbilical cord endothelial cells (HUVEC)
HUVEC were incubated with NST301-C or NST302 or buffer alone and then with streptavidin-FITC. For each treatment, the percentage of cells that were stained with FITC was determined. The graph shows mean values +S.D. obtained from three independent experiments.

Figure 4:
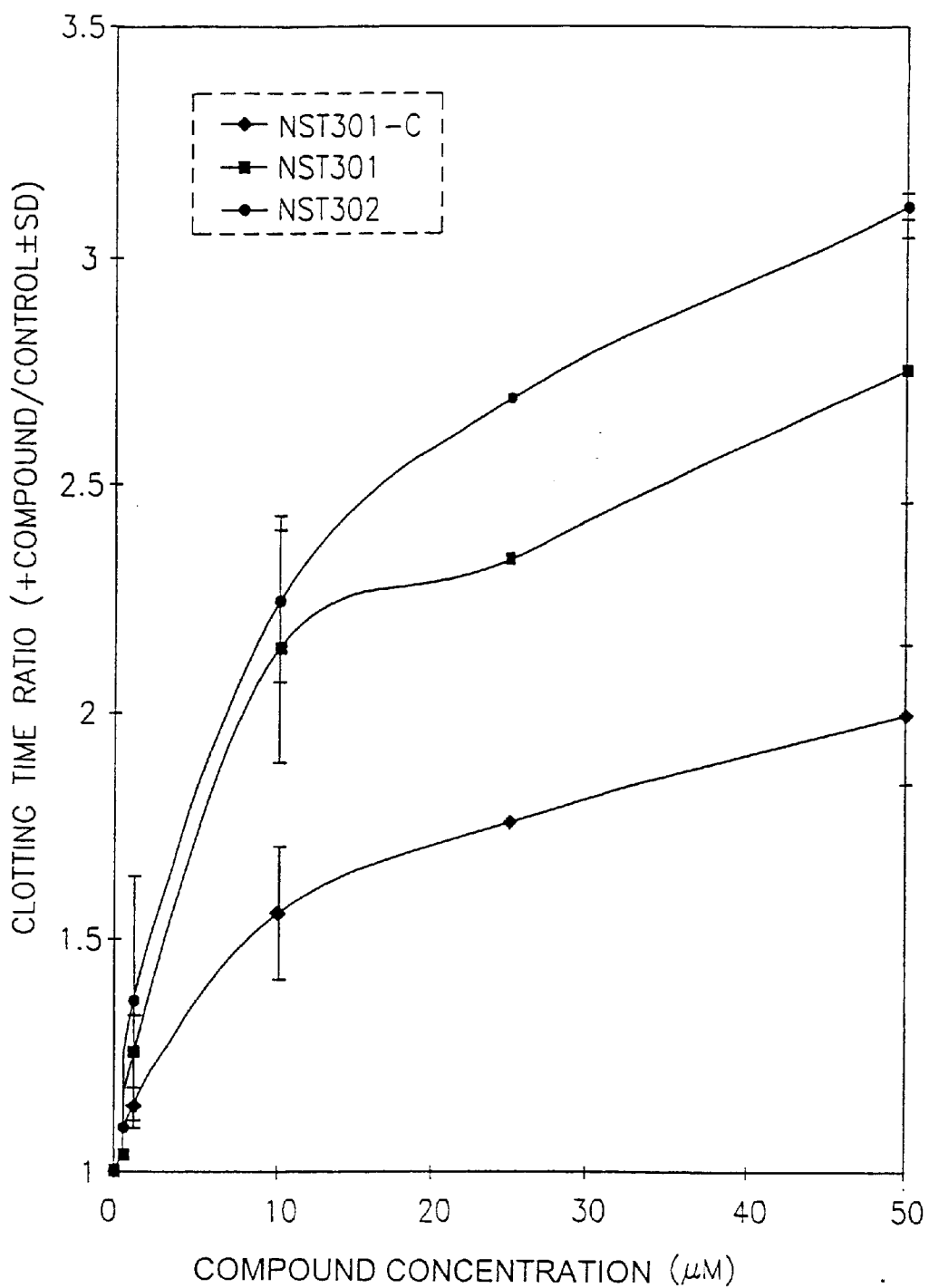
FIG. 4 Anticoagulant effect of NST300 compounds; Russell viper venom (RVV) test.

FIG. 4. Anticoagulant effect of NST300 compounds; Russell viper venom (RVV) test.

Inhibition of Russell viper venom (RVV)-mediated clotting was measured for NST300 compounds. Clotting time ratio was calculated as the ratio of clotting time measured with normal plasma,pretreated with NST300 compounds, versus clotting time measured with non-treated normal plasma. The compounds manifested anti-coagulant effects, with NST302 exerting the most powerful effect. The graph represents 3 independent experiments.

FIG. 5: NST300 compounds inhibit the pro-coagulant activity of apoptotic cells

Figure 5A:
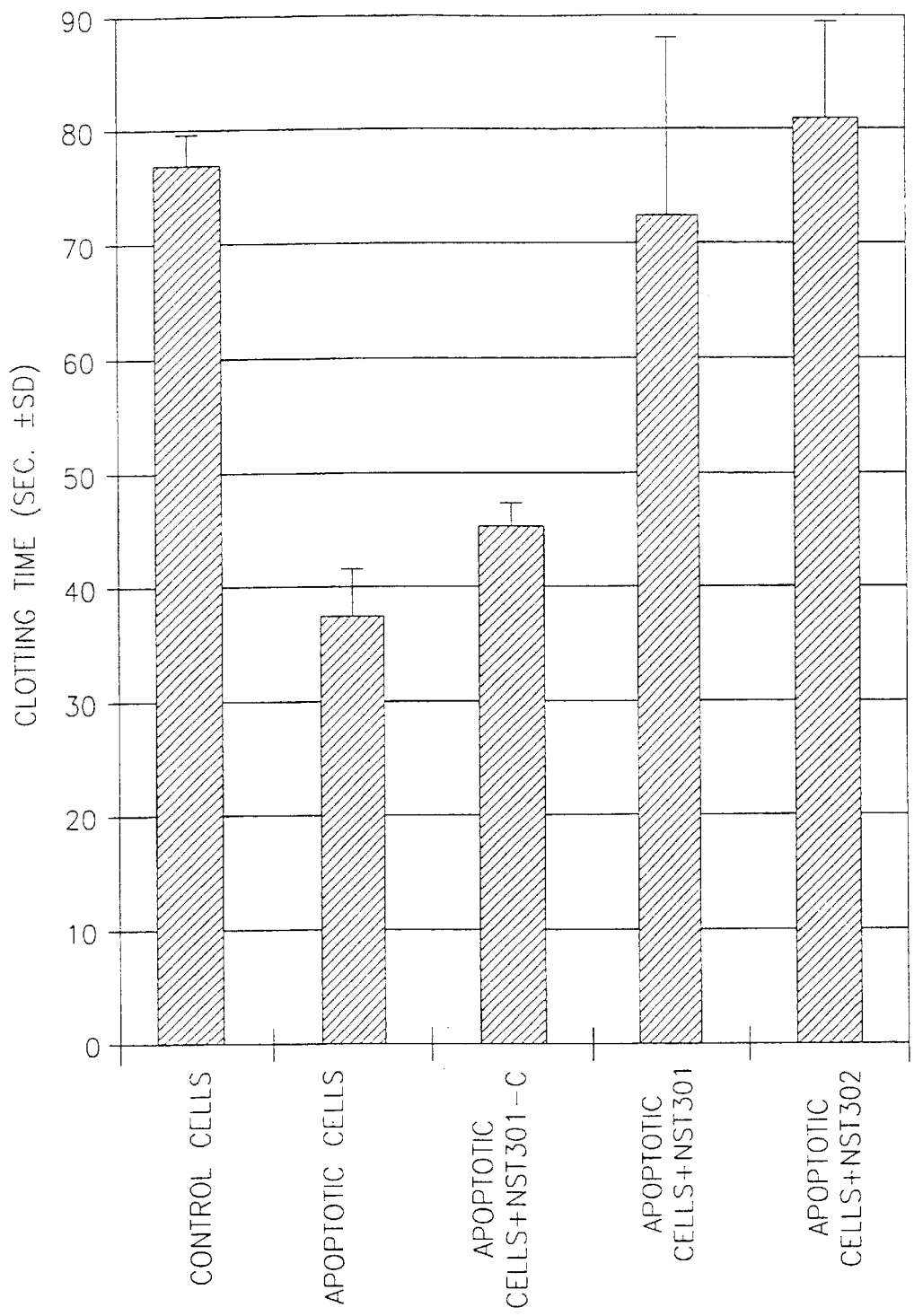
FIG. 5a: Anticoagulant effects of NST300 compound; modified APTT test.

FIG. 5a: Anticoagulant effects of NST300 compound; modified APTT test

A modified APTT coagulation test was used to determine the procoagulant activity of apoptotic cells. Samples of control non-apoptotic cells and apoptotic cells were used with or without preincubation with NST300 compounds, at a concentration of 0.5 $\mu$M. Reactions were performed in duplicates, and the graph represents 3 independent experiments.

NST301 and NST302 were potent in fully reversing the marked procoagulant effect of the apoptotic cells. By contrast, only a very modest effect was exerted by the control compound NST 301-C. Reference is being made to the descriptions in Examples 2 to 4.

Figure 5B:
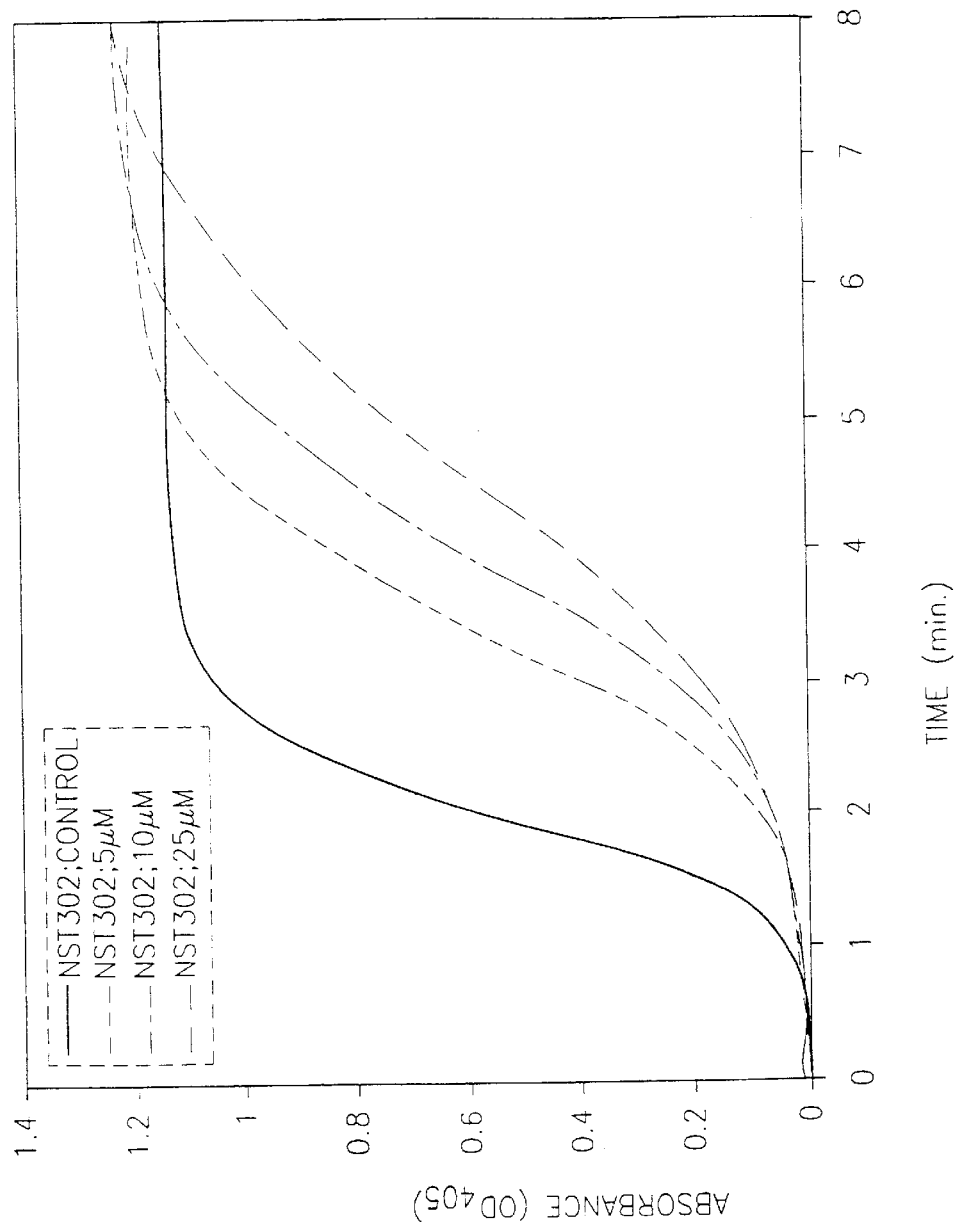
FIG. 5b: NST302 compound inhibits thrombin generation mediated by apoptotic cells.

FIG. 5b NST302 compound inhibits thrombin generation mediated by apoptotic cells:

NST302 inhibits thrombin generation mediated by apoptotic cells. A thrombin generation assay was used to demonstrate the pro-coagulant activity of apoptotic cells.

Samples of procoagulant cells (apoptotic Hela cell, treated wish 500 $\mu$M of DA for 18 hours) were used with or without pre-incubation with different concentrations (5–25 $\mu$M) of NST302. Inhibition of thrombin generation is observed already in the presence of 5 $\mu$M of NST302. The effect of NST302 is dose dependent.

FIG. 6: NST302 inhibits binding of derived from SLE (Systemic Lupus Erythematasus) patients (lupus plasma) to anionic phospholipids.

Figure 6A:
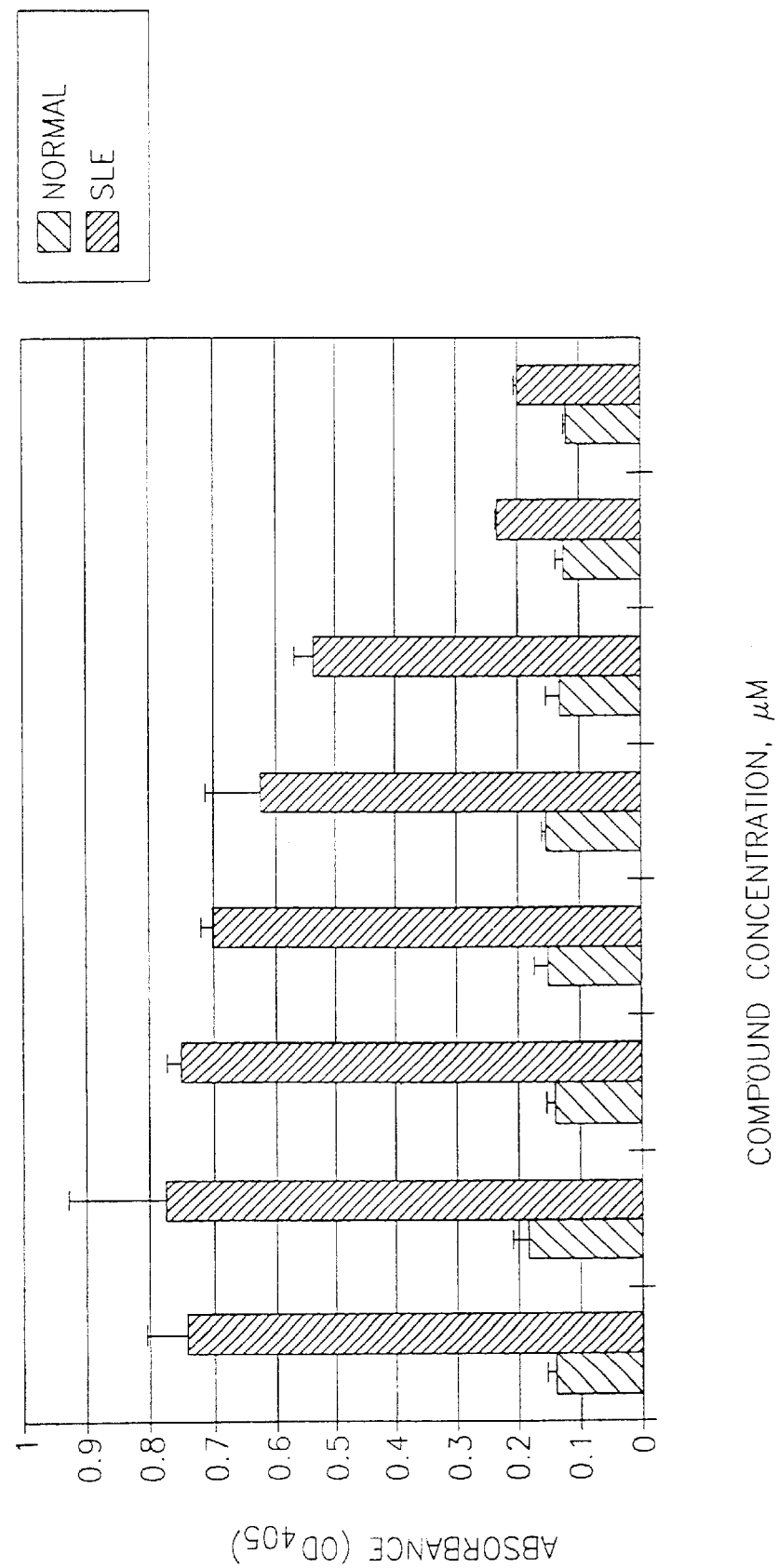
FIG. 6a: NST302 compound inhibits binding of lupus plasma (from source A) to CL.
Figure 6B:
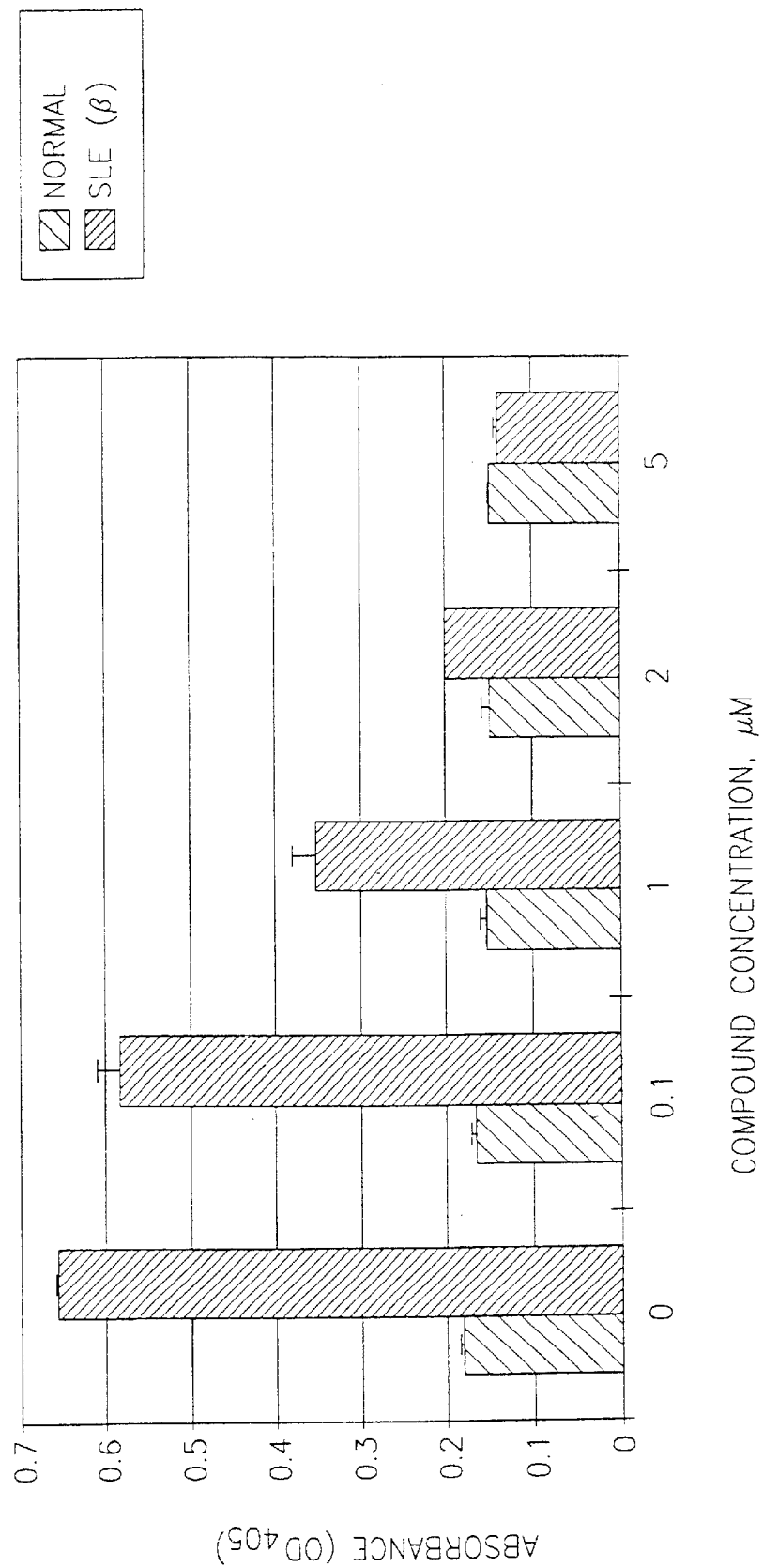
FIG. 6b: NST302 compound inhibits binding of lupus plasma (from source B) to CL.

FIGS. 6a & 6b: NST302 compound inhibits binding of Lupus derived plasma to CL.

Binding of normal and Lupus patients plasma to CL coated ELISA wells in the presence of increased concentration of NST 302 compound.

FIG. 6a: Lupus patients plasma commercially available from Gradipore Inc.

FIG. 6b: Lupus patients plasma commercially available from Biopool Inc.

The columns represents the relative amount of Lupus or normal plasma molecules that bind to the cells. Dramatic displacement of binding of Lupus plasma (derived from different sources) from the CL coated plates is demonstrated. Values are expressed as optical density units (OD). Mean±SD of duplicate wells. A representative experiment out of three.

Figure 6C:
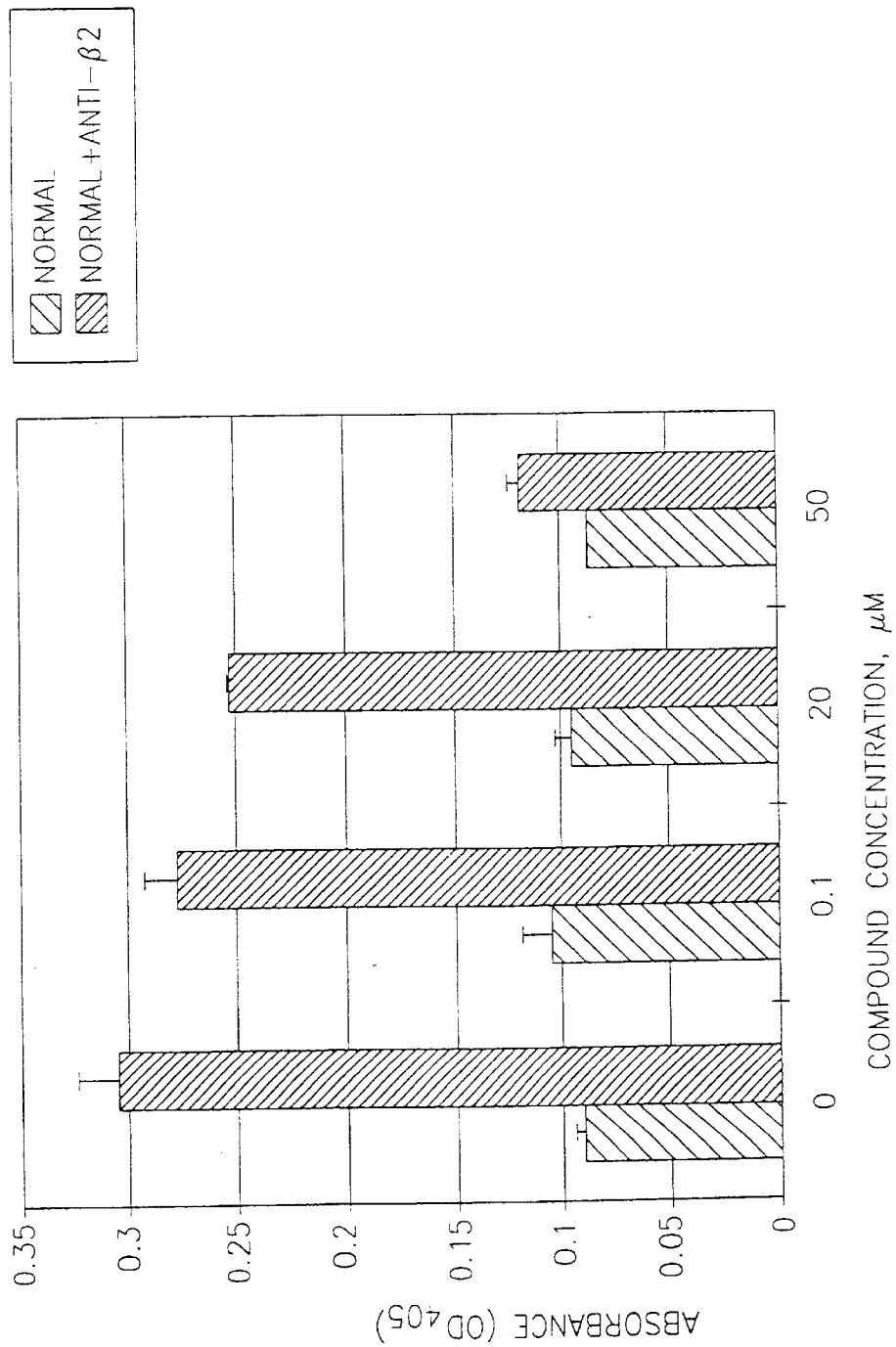
FIG. 6c: NST302 compound competes with anti β2GPI for binding to CL.

FIG. 6c: NST302 compound competes with anti β2GPI for binding to CL

Competition between NST 302 compound and anti β2GPI for binding to CL coated wells was performed in ELISA assay. CL coated wells were incubated with increased concentrations of NST 302 compound in the presence of anti β2GPI and 10% normal plasma. The columns represents the relative amount of anti β2GPI molecules that bind to CL. Complete inhibition or anti β2GPI binding to CL is evident in the presence of NST302 compound. Values are expressed as optical density units (OD). Mean±SD of duplicate wells. A representative experiment out of three.

Figure 6D:
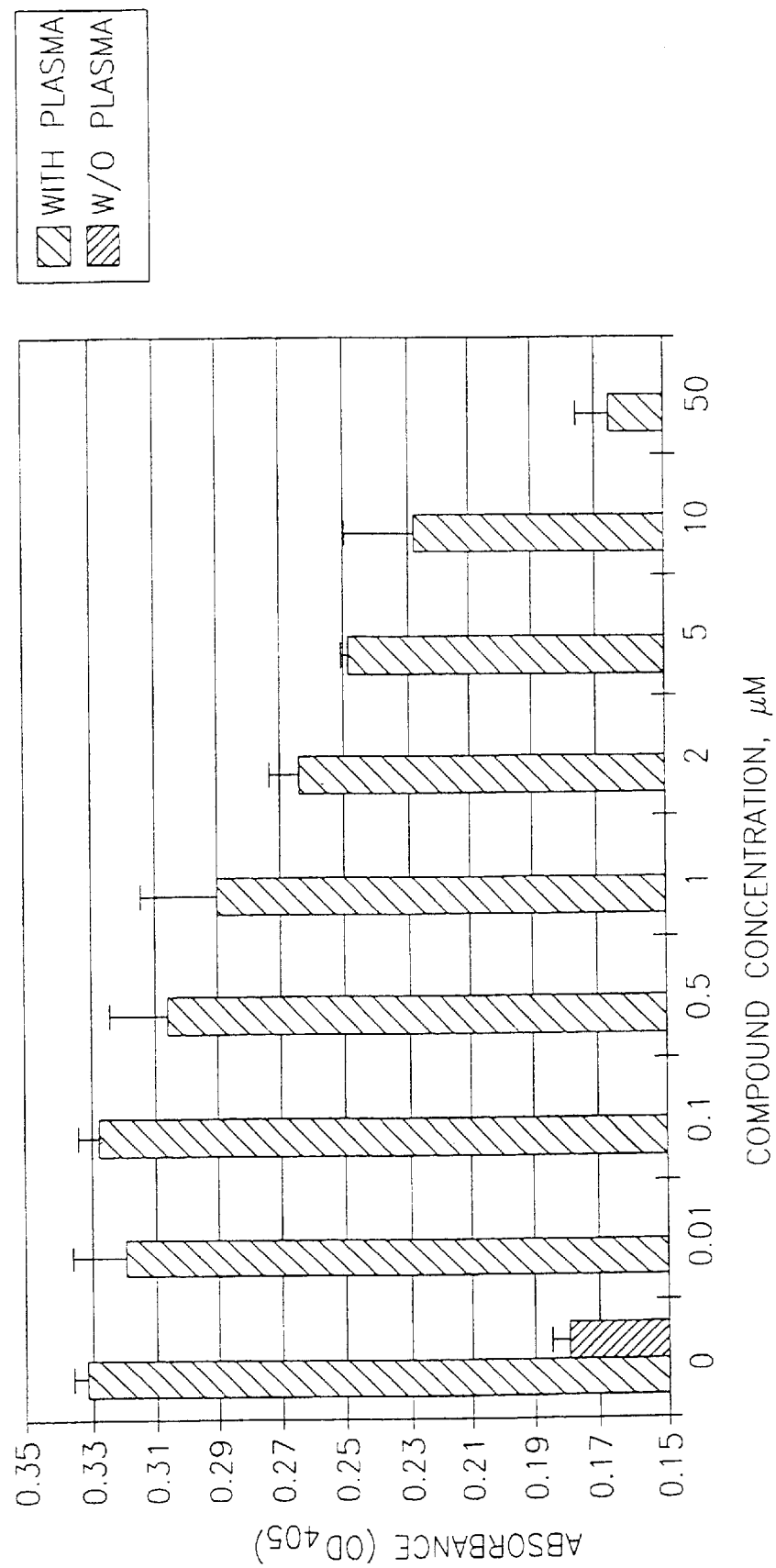
FIG. 6d: NST302 compound competes with anti β2GPI for binding to HUVEC cells.
Figure 6E:
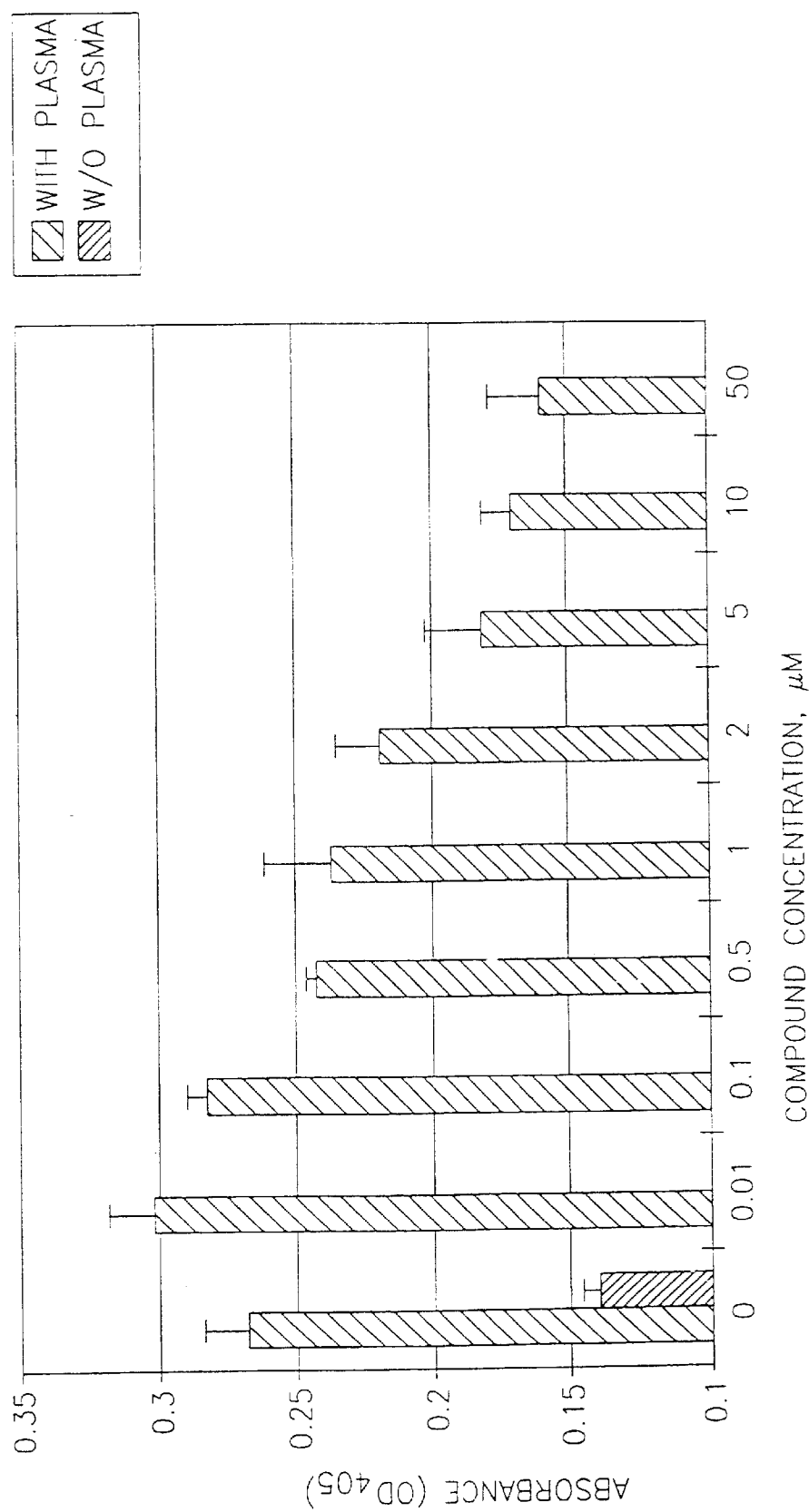
FIG. 6e: NST302 compound competes with anti β2GPI for binding to BeWo cells.

FIGS. 6d & 6e: NST302 compound competes with anti β2GPI for binding to HUVEC or to BeWo cells.

Competition between NST 302 compound and anti β2GPI for binding to HUVEC and BeWo cells was performed in a modified ELISA assay. Cells were plated in a 96 tissue culture plate. Following 18 hours incubation the wells were incubated with increasing concentrations of NST 302 compound and anti β2GPI in the presence of 10% normal serum. The columns represent the relative amount of anti β2GPI molecules that bind to the cells.

FIG. 6d. HUVEC cells.

FIG. 6e. BeWo cells.

Using both cell types, NST302 exhibit dramatic and significant ability to block binding of Lupus derived plasma to the pro-coagulant surface of cells. Values are expressed as optical density units (OD). Mean±SD of duplicate wells. A representative experiment out of three.

Figure 7:
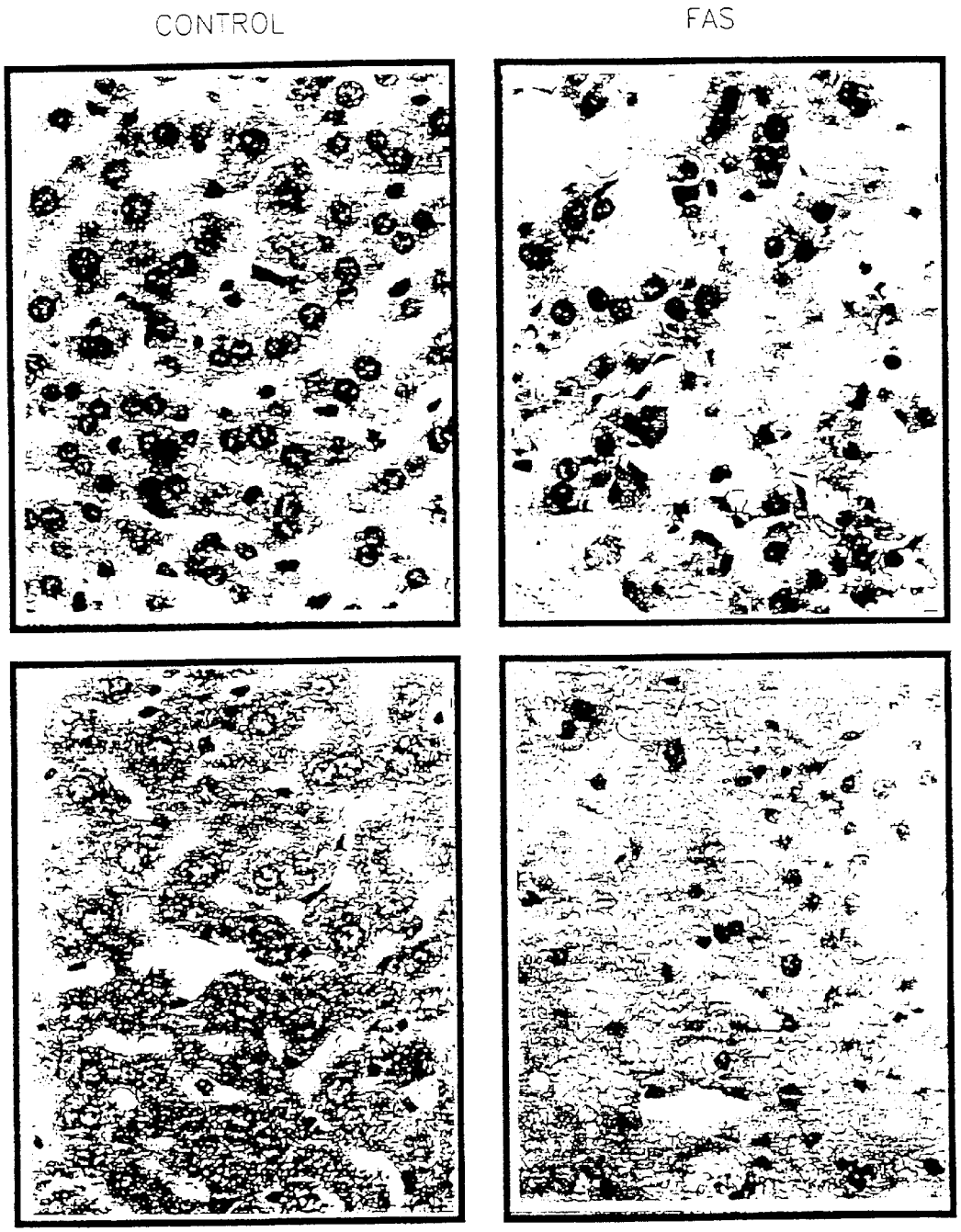
FIG. 7: Induction of Fas mediated apoptosis in vivo, in mouse liver.

FIG. 7: Induction of Fas mediated apoptosis in vivo, in mouse liver

Control non-treated animals were prepared for histological analysis of the liver section and stained with Hematoxylin and Eosin (a) or with TUNEL (c). Anti Fas injected animals were prepared as above for Hematoxylin and Eosin (b) or with TUNEL (d). Two hours after intravenous administration or anti-Fas antibody, typical features of apoptotic events appears such as advanced chromatin condensation, nuclei crescent shaped, nuclear pyknosis and cell fragmentation (arrow pointing apoptotic hepatocyte). Many red blood cells penetrate the liver and changes were also focally associated with hemorrhage (FIG. 7b) in the entire lobule. Magnification is x400.

Figure 8:
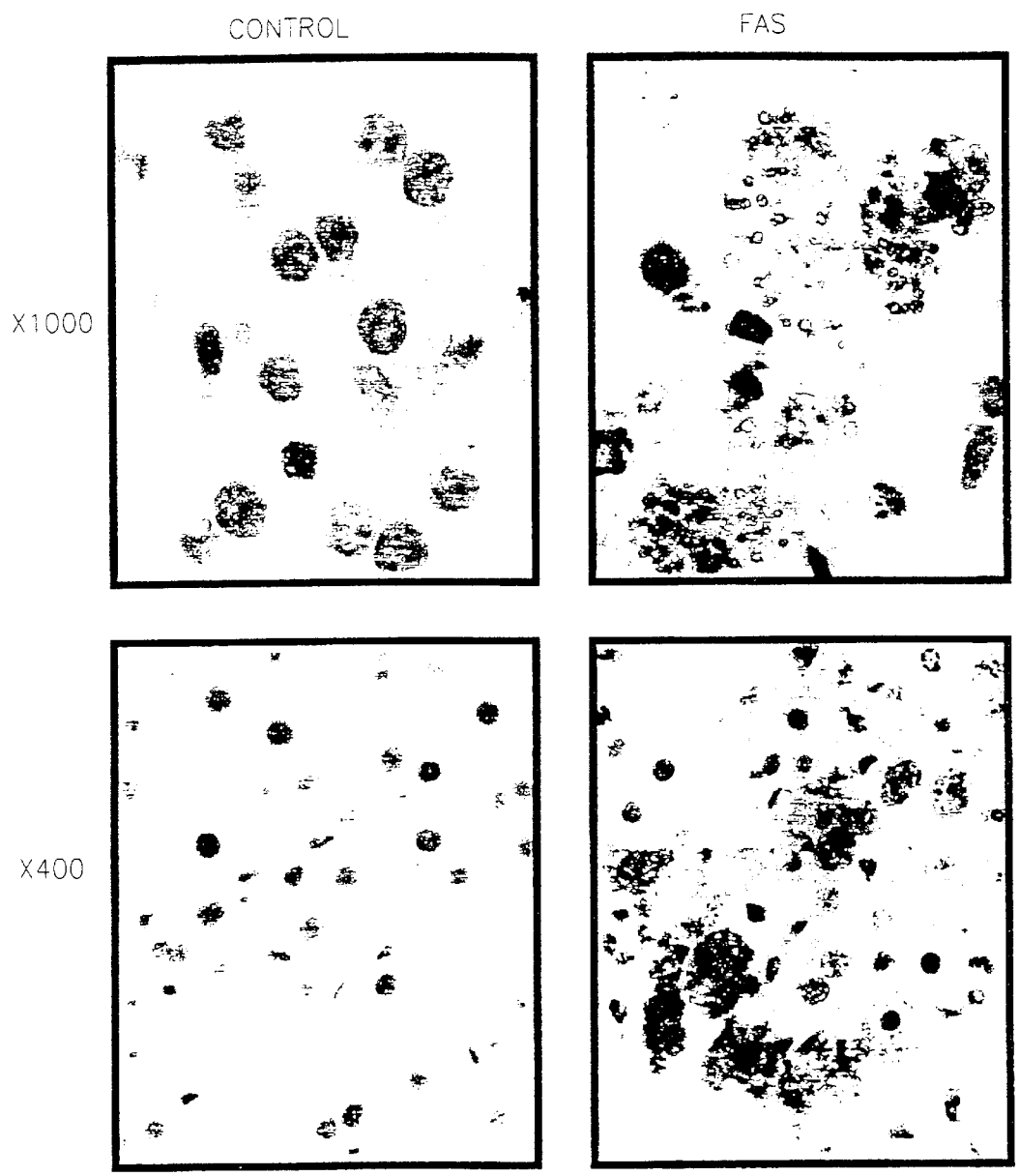
FIG. 8: Staining of apoptotic cells in vivo with NST302.
Figure 9A:
FIG. 9: Staining of apoptotic cells, in vivo, with NST302; Pharmacokinetics studies.
Figure 9B:
Figure 9C:
Figure 9D:
Figure 9E:
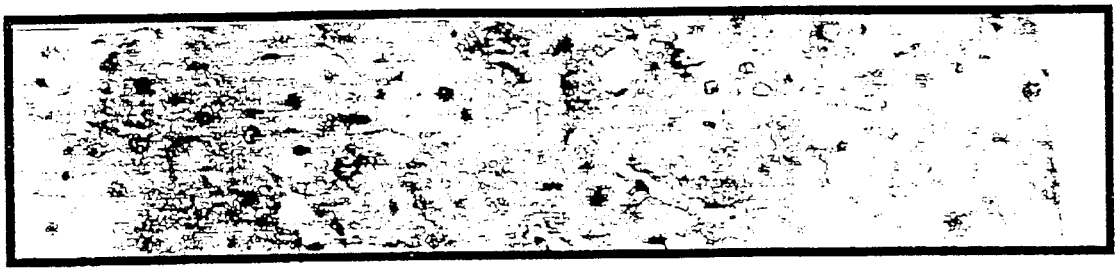
Figure 9F:
Figure 9G:

FIG. 8: Staining of apoptotic cells in vivo with NST302

NST302 staining (brown immunostaining product) is observed at cytoplasma and cytoplasmatic border of apoptotic hepatocytes. (a and c): control non-treated animals, stained with NST302 compound, at a concentration of 5 $\mu$M.

(b and d); Anti Fas treated animal, stained with NST302 compound as above.

Magnification is times 1000 (for a and b) and times 400 (for c and d).

FIG. 9: Staining of apoptotic cells, in vivo, with NST302; Pharmacokinetics studies The appearance and disappearance of the compound NST302 from the liver following its injection to mice. Animals treated or untreated with anti-Fas antibody were injected with the NST302 compound, and its detection was tested 5, 15, 20, 30, 60, 90, 120 min after its injection.

(a): Five minutes after the injection of NST302, an early distribution of the molecule, can be observed in both treated and non-treated animals.

(b and c): Staining appears to peak after 15–20 minutes from the time of the injection of NST302 compound only in mice treated with anti-Fas antibody.

(d–f): staining of apoptotic cells with the NST302 compound slowly declined, when the liver was sectioned 30,60 and 90 minutes after NST302 injection (g): Two hours after the injection of the NST302 compound no staining was detected.

Magnification is ×200.

EXAMPLE 1

Synthesis of NST301:

Myristate-GGGKKKKKRFSFKKSFKLSGFSFKKNKKK (SEQUENCE ID NO. 3)(Biotin)-OH.

Loading of Lys(Mtt) on Solid Support 2.37 gr of 9- fluorenylmethoxycarbonyl (Fmoc)-Lys-(Mtt)-OH were dissolved in dichloromethane (DCM) 785 mg of N,N'dicyclohexylcarbodiimide (DCC) were added following the addition of 46 mg of dimethylaminopyridine (DMAP). Then, 2 gr of Wang resin (0.95 mmole/gr.) were added and the reaction solution was stirred at room temperature for 2 hr. Then, the loaded resin was washed with DCM and N-methyl pyrrolidone (NMP) and then recoapled under the same conditions using half quantities of reagents. The resin was then washed and dried in vacuum. 3.18 gr. of loaded resin were obtained.

Preparation of Lys (Biotin)-Resin

Fmoc-Lys (mtt)-Resin was stirred with a mixture of 1% trifluoroacetic acid (TFA) and 0.1% triisopropylsilane (TIS) in DCM at 0° C. for 30 min and then for one hour at room temperature. Then, the resin was washed with NMP and DCM, and dried in vacuum. 2.68 gr. of loaded resin were obtained. This resin was then swelled with 25 ml NMP in the Presence of 930 mg Biotin, 1.44 gr. O-benzotriazole-N,N,N',N'-tetramethyl-uronium-hexafluophosphate (HBTU), 513 mg N-hydroxybenzotriazole (HOBt) and 1 ml of diisopropylethylamine (DIEA). The reaction was stirred for 4.5 hr. Then, the resin was washed with NMP and DCM, and dried in vacuum. 2.8 gr. of Fmoc-Lys(Biotin)-resin were obtained.

Fmoc-Lys (Biotin)-Resin was used as starting material for the preparation of Myristate-GGGKKK-KKRFSFKKSFKLSGFSFKKNKKK(Biotin)-OH. The synthesis was accomplished using an AB1 433A peptide synthesizer (Applied Biosystems U.K.) with HBTU/HOBt coupling reagents. Protected amino acids were introduced into the growing peptide-resin one after the other. The amino acids used were Fmoc-N$^\alpha$ protected. Trifunctional amino acids were side chain-protected as follows: Arg-2,2,5,7,8-pentamethyldihydrobenzofuran-5-sulfonyl (Pbf), Ser-tert-butyl(tBu), Lys-tertbutoxycarbonyl (Boc), Asn-trityl (Trt). Each Fmoc amino acid was activated in situ using a 1:1 HBTU/HOBt mixture and subsequently coupled to the resin for 50 min. DIEA was used during coupling as a non-nucleophilic base. The Fmoc protecting group on the amine was then removed with 20% piperidine in NMP for 20 min. Three equivalents of the activated amino acids and coupling reagents (HBTU and HOBt) were employed in the coupling reactions. The deprotection and coupling steps were repeated with the addition of each subsequent amino acid until the peptide synthesis was completed. The final amino acid was deprotected using 20% piperidine in NMP, and coupled with myristic acid under the same conditions as used for the introduced amino acids. The peptide-resin was washed with NMP, followed by DCM, and dried in vacuum. 562.5 mg of peptide resin were obtained.

Cleavage From the Solid Support

A cleavage mixture consisting of TFA 95% and TIS 5% was added to the peptide-resin (20 ml of cleavage mixture to 1 gr. resin). The solution was stirred at room temperature for 60 min. The resultant slurry (resin) was filtered using a sintered glass filter. The resin was washed twice with TFA. The filtrate was concentrated to a volume of 1 ml using a stream of nitrogen. Following the addition of cold diethyl ether (20 ml), the solution was cooled on ice bath. After 60 min., the peptide was precipitated by centrifugation, washed with cold ether and dried in vacuum. 383.7 mg of crude peptide were obtained.

Purification and Characterization

Peptide was purified by RP-HPLC on $C_{18}$ 5$\mu$ of a Phenomenex Kromasil column (10 mm I.D.×25 cm). Samples were eluted using the following gradient:

A. distilled $H_2O$/0.05% TFA; $\lambda$=214 nm; B. acetonitrile 0.05% TFA,=214 nm; flow 5 ml/min. The extent of purity of each peptide was monitored by rechromatography on $C_{18}$ 5 $\mu$m of Phenomenex Kromasil (4.6 mm I.D.×25 cm) analytical column, flow 1 ml/min. The characterization of the peptides was performed by Electrospray-Mass spectra (ES-MS). After purification, peptide was obtained at 91.5% purity (non calibrated RP-HPLC, acetonitrile/water 0.1% TFA gradient from 5% to 50% acetonitrile at 30 min. MS (ES) calcd. m/z for $C_{183}H_{304}N_{48}O_{38}S_1$ (MH+) 3814.3, found 3816.2 (double charged).

Synthesis of NST302, and NST301-C:

The same method as described for NST301 was also successfully and repeatedly used or the synthesis of NST302 and NST301-C, respective of the appropriate sequence of each compound. This further exemplifies the applicability of the above method of synthesis as a general method for synthesis of NST300 compounds.

After purification, the NST302 peptide was obtained at 85.7% purity (non calibrated RP-HPLC, acetonitrile/water 0.1% TFA gradient from 10% to 35% acetonitrile at 30 min. MS (ES) calcd. m/z for $C_{177}H_{295}N_{45}O_{35}S_1$ (MH+) 3644.6, found 3644.6 (double charged).

EXAMPLE 2

NST301 and NST302 as Markers for the Detection of Cells Undergoing a Death Process.

Re-distribution of anionic phospholipid molecules from the inner leaflet of the plasma membrane to the outer leaflet is one of the early events occurring in apoptotic cells. NST300 compounds are designed to be used as early detectors of CMLA loss. In order to test the ability of NST300 compounds to recognize charges in CMLA during cell death, the binding of NST301 and NST302 to cells undergoing apoptosis was measured. Endothelial cells represent cell populations that naturally expose anionic phospholipide on their plasma membrane. The binding of NST300 compounds to endothelial cells was also measured.

Two modes of binding detection were used: the first mode demonstrates the binding to single cells by fluorescent microscopy, and the second mode demonstrates the binding to populations of cells by flow cytometric analysis.

EXAMPLE 2A

Detection of Binding of NST300 Compounds to Single Apoptotic cells; Fluorescent Microscopy.

Said compounds NST301 or NST302, labeled with biotin as a marker (at the $X_5$ domain, see FIG. 1) were used to study their binding to apoptotic cells. Said compounds were each dissolved in TBS (Tris Buffered Saline; 10 mM Tris PH 8.0; 150 mM NaCl), at a stock concentration of 10 mM.

(a) Preparation of Apoptotic Cells.

HeLa S3 cells (ATCC CCL-2.2) were cultured on a glass chamber slide (Nunc) on a culture area of 0.8 cm$^3$. Chamber slides were pre-coated with 1% gelatin (Sigma) Cells were seeded at a density of 8×10$^4$ cells/chamber, in a volume of 300 $\mu$l of culture medium [Dulbecco's Modified Eagle's Medium (DMEM) supplemented with 2 mM of L-Glutamine; 100 units/ml of Penicilin; 100 μg/ml of Streptomycin; 12.5 units/ml of Nystatin and 10% of Fetal Calf Serum (FCS)]. Following 24 hours of incubation the cells were treated with an apoptotic trigger [i.e. dopamine (DA), which is a well characterized model of apoptosis (Lou et al., J. Biol. Chem. 1998; 273:3756–3764)].

For the DA treatment, the culture medium was replaced by a low serum containing medium (2% FCS), with 500 μM of dopamine (from RBI, Mass., USA) for 18 hours.

(b) Evaluation of Apoptosis

The evaluation was performed by staining with Hoechst 33342 dye (Molecular probes). This blue fluorescent dye is rapidly permeable into cells and stains DNA. Hoechst 33342 was added to growing cultures at a concentration of 1 μg/ml and 20 minutes later, the cells were visualized under UV light microscopy. The relative number of apoptotic cells with condensed or fragmented chromatin was then evaluated and compared with non-apoptotic cells which characteristically show a pale and diffuse staining. Photomicrographs were taken for documentation. An example of detection of apoptosis by Hoechst 33342 staining can be seen in FIG. 2A (c). This method was used to evaluate the level of apoptosis in cultured cells prior to binding to the NST300 compounds. Cultures that exhibited at least 50% of apoptosis following DA treatment were taken for further analysis.

(c) Binding of NST301 and NST302 to Cells Undergoing Apoptosis.

Apoptotic, as well as control untreated cells were grown as specified above and washed twice with TBS. The slides were then incubated with the NST300 compound at concentrations of 250–750 nM for 60 minutes, in a total volume of 100 μl. Slides were then dipped into a Couplin Jar containing 50 ml of TBS, and then incubated with 50 ng/ml of a sterptavidin reagent labeled with FITC (Fluorescein Isothiocyanate Conjugated, from Jackson Immunolaboratory U.S.A.). Incubations were performed for 15 minutes at room temperature, in a final volume of 100 μl. The slides were then washed with TBS as above and were then mounted with Fluoroguard antifade reagent (from Biorad Calif., USA).

The binding was then evaluated with a fluorescent microscope (IX70; Olympus), using a NIBA filter (Narrow Interference Blue A from Olympus).

FIG. 2a demonstrates the DA-induced apoptotic process in HeLa cells, and exhibits a typical culture with 50% of the cells undergoing apoptosis, as can be identified by Hoechst 33342 staining.

FIG. 2b demonstrates the binding of a NST301 compound to cells undergoing DA-induced apoptosis. Strong staining of cells is evident.

FIG. 2c indicates the staining of apoptotic cells in various stages of the death process. Staining ranged from mild peripheral membrane staining of the cells in the early stages of apoptosis to intense staining of the more-advanced apoptotic cells.

The compound NST302 exhibited a similar staining profile.

Non-treated cells served as control and did not show significant labeling by NST compounds. NST301-C also served as a control. This compound did not show any significant binding to the cells.

This example shows that NST300 compounds can serve as potent detectors of apoptotic cells and associated membrane alterations.

EXAMPLE 2B

Detection of Binding of NST300 Compounds to Apoptotic Cells by FACS Analysis (a) Preparation of Apoptotic Cells for FACS Analysis HeLa cells were plated on tissue culture plates at a density of $3 \times 10^6$ cells/10 cm dish, and grown in a DMEM medium containing 10% FCS, as described in A. The cells were then incubated at 37° C. overnight, and then the medium was replaced with a medium containing 2% FCS and 500 μM of dopamine. 18 hours later, the medium was aspirated and discarded, and 10 ml of Phosphate Buffered Saline pH 7.4 (PBS) were added to the culture dish. The cells which were detached from the culture dish into the PBS were collected. These cells represent advanced apoptotic cells. The remaining cells which were attached to the culture dish were trypsinized by the addition of 2 ml of trypsin for 2 minutes at 37° C., followed by the addition of 10 ml of a medium containing 10% of FCS. The cells were then washed with PBS containing 2% Bovine Serum Albumin (BSA), and resuspended in TBS containing 2% BSA (TBS-BSA). These cells were regarded as early apoptotic cells. Non-treated cells served as controls, and were subjected to similar treatments as above. Only non-treated cells that were attached to the culture dish were used as control cells for the FACS analysis.

(b) Binding of NST Compounds to Cells Undergoing Apoptosis: Preparation for FACS:

The binding of compounds (NST301 and NST302) and of control compound (NST301-C) to samples of $5 \times 10^5$ cells was tested. A set of 3 different cell types was taken:
Control non-treated cells;
Early apoptotic cells; and
Advanced apoptotic cells.
Each of the three types of cells was tested for binding to:
Compounds NST301 or NST302;
Control compound NST301-C; and
No compound (FITC only).

The incubation with the NST300 compounds or control compound was performed in a final volume of 100 μl TBS-BSA, 5 μg/ml of propidium iodide (PI) and 750 nM of the tested compound or the control compound.

PI is a red fluorescent dye that stains DNA. It does not cross the plasma membrane of cells that are viable or cells that are in the early stages of apoptosis, since they maintain the plasma membrane integrity. Only cells that are in advanced apoptotic stages, or cells that have already died by apoptosis or necrosis will be permeable to PI and will be stained with the dye. The reactions were incubated at room temperature for 15 minutes and then collected by centrifugation at 1000×g for 3 minutes. The cells were then washed in 500 μl of cold TBS-BSA and centrifugated as before. The cells were then suspended in 100 μl of TBS-BSA containing streptavidin conjugated to fluorescein (FITC). The incubation was performed for 15 minutes at room temperature in the dark. Thereafter, the cells were washed three times in TBS-BSA and were taken for FACS analysis.

(c) FACS Analysis

The FACS analysis was performed on a Beckton-Dickinson cell sorter, using lysis II software. Excitation was at 488 nm and the emission or FITC detection was at 535 nm and for PI detection at 585 nm.

FIG. 3a demonstrates the binding of NST300 compounds to two different cell populations: early apoptotic cells, in comparison to control non-apoptotic cells. When each one of these cell populations was stained by FITC and PI only, with no compound, only a marked increase of PI staining was observed as a function of advancement of the apoptotic process.

Staining with FITC-labeled NST301 demonstrated that the population of early apoptotic cells was stained strongly with the compound. Only 43% of these cells were double stained also with PI (indicative of advanced apoptotic cells).

Staining with the control compound NST301-C indicated residual binding of this compound to either one of the two different cell populations, similarly to the control examples of staining with PI and FITC only, but without the compound. These results indicate that NST301 can specifically bind to apoptoic cells at the early stages of the death process, and therefore can be used as detector of early apoptosis.

The NST302 compound was used in similar binding experiments in order to determine its binding to apoptotic cells, and in order to compare its performance to the binding of NST301. When apoptotic cells were exposed to 750 nM of each one of the NST compounds, a higher binding intensity (measured as the FITC mean value) was measured for NST302 (FIG. 3b) indicating that NST302 is more potent than NST301 in detecting apoptotic cells.

The ability of the NST301 compound to detect populations of early apoptotic cells was further emphasized by the analysis performed in FIG. 3c, in which the ratio between total FITC binding versus total PI binding was used as a variable to define the potential of the NST301 compound to bind to early apoptotic cells. A high FITC/PI ratio thus indicates that most of the cells in a given population bind NST301 whilst their plasma membrane is still intact. Early apoptotic cells had a higher FITC/PI value (2.2) as compared to a population of advanced apoptotic cells (having a value of 1.2). These values were dramatically higher than the FITC/PI values obtained for the same cellular populations when exposed only to PI and FITC, or when exposed to PI and the control compound NST300-C (FIG. 3c). These data therefore further exemplify the potency of the NST301 compound as a detector of early apoptosis.

EXAMPLE 2C
NST302 as a Marker for Cells Exposing Anionic Phospholipids, FACS Analysis.

Human Umbilical Vein Endothelial Cells (HUVEC) normally express anionic phospholipids on their outer membrane (Van Heerde W L et al., 1994, Biochem J. 302, 305–312), therefore they can serve as a target for binding of NST300 compounds. Binding detection was done using flow cytometric analysis to populations of HUVEC cells.

(a) Preparation of Cells for FACS Analysis:

HUVEC (CC-2517, obtained from Clonetics, Walkersville, Md.) were grown on tissue culture flasks in Endothelial cell medium (EGM-2 Bulletkit, CC 3162, Clonetics). Mid-confluent cultures were harvested using Trypsine/EDTA solution (CC-5012, Clonetics). The cells were rinsed twice with PBS containing 2% BSA and kept on ice. Samples of $10^6$ cells were tested for binding. The incubation with NST300 compound was performed in a final volume of 100 ml TBS+2% BSA containing 500 ng of NST302 or NST301-C or no compound.

The reactions were incubated at room temperature for 40 minutes and then 400 µl of TBS-BSA were added and cells were collected by centrifugation at 3000×g for 3 minutes. Cells were washed in 1 ml of TBS-BSA and centrifuged as before and then suspended in 100 µl of TBS-BSA containing streptavidin conjugated to flourescein (FITC) for detection of the bound biotinylated compound. Incubation was for 15 minutes at room temperature in the dark. Thereafter, 400 µl of TBS-BSA were added and cells were centrifuged and washed again with 1 ml of TBS-BSA as before and then resuspended in 400 µl of TSS and taken for FACS analysis.

(b) FACS Analysis

The FACS analysis was performed on Beckton-Dickinson cell sorter, using lysis II software. Excitation was at 488 nm and emission for FITC detection was a 535 nm.

A dot plot analysis was done for each treatment. Dot plot showing FITC binding (FL1) versus cell size (FSC), shows the fraction of FITC binding cells that is indicative of binding of NST300.

FIG. 3d demonstrates binding of NST302 to HUVEC. About 70% of the cells incubated with NST302 were FITC positive while only 7% of the cells incubated with the control non-myristylated compound NST301-C were FITC positive.

These results demonstrate the ability of NST302 to bind to cells exposing anionic phospholipids on their plasma membrane.

EXAMPLE 3
NST301 and NST302 Compounds as Potent Anti-coagulants: Inhibition of Clotting Induced by Negatively Charged Phospholipids.

In physiological conditions, as well as in a standard coagulation assay, anionic phospholipid molecules serve as a potent catalytic surface on which binding of various coagulation factors takes place, thus catalyzing among others, the assembly of the prothrombinase complex (Mann K G, et. al. Blood 1990; 76:1–16).

The ability of NST300 compounds to inhibit coagulaton catalyzed by negatively—charged phospholipids was evaluated in a standard coagulation test of the Russell viper venom (RVV) assay. The RVV reagent directly activates factor x present in the plasma, thus promoting prothrombinase complex formation. This reagent is widely used as a standard phospholipid responsive clotting test. (Thiagarajan et al., Blood, 1986; 869–874).

The RVV reagent kit, containing RVV and negatively charged phospholipids, from Gradipore, Australia was used. The reactions were started by mixing 100 µl of RVV reagent, and 100 µl of quality control plasma collected from normal individuals (commercially available from Instrumentation Laboratory, Italy). Clotting time was determined as the time-point beyond which the continuously mixed reaction ingredients in the test tube, could no longer be aspirated with a pasteur pipette. Clotting time was measured independently by two separate researchers.

Clotting time was measured following addition of NST301 or NST302 compounds (at concentrations between 0.5–50 µM) to the above reaction mixture.

FIG. 4 demonstrates the effect of NST300 compounds on the clotting time as measured in the above RVV test. A concentration-dependent binding curve for each one of the compounds is shown. The control clotting time, when no compound was added to normal plasma was 40 seconds. NST301 and NST302 markedly and significantly increased the clotting time by a factor of 2.6 and 3.1, respectively, as compared to control. (p<0.001, Student's test). $EC_{50}$ (effective dose of 50%) for these compounds in the paradigm used in this experiment was 5–10 micromolar.

Significant, though moderate effect, was also observed with the NST301-C compound. NST302 was more potent as an anti-coagulant than NST301. These experiments therefore show that NST300 compounds are potent anticoagulants.

EXAMPLE 4
NST300 Compounds Act as Anticoagulants NST300 Compounds Potently Correct the Procoagulant Effects of Apoptotic Cells.

During the early stages of apoptosis, loss of plasma membrane asymmetry occurs, leading to the exposure of anionic phospholipids on the outer plasma membrane. As a result, apoptotic cell surfaces can serve as procoagulants (Casciola-Rosen et al., J. Proc. Nat. Acad. Sci. 1996;93:1624–1629; Flynn P D et al., Blood 1997; 89:4378–4384). The procoagulant activity of apoptotic cells was demonstrated using a modified APTT (Activated Partial Thromboplastin Time) coagulation assay.

In the standard APTT test, clot formation is triggered by recalcification of plasma and addition of cephalin, i.e. negatively-charged phospholipids. Time until clot formation was measured as described in Example 3. When normal control plasma and cephalin were used, clotting was observed after 40 seconds. In the modified APTT test, used in the present study, the addition of negatively-charged phospholipids (cephalin) was replaced by addition of apoptotic cells.

The results are presented in FIG. 5a HeLa S3 cells were treated with 500 $\mu$M of dopamine for 18 hours. The cultured medium was discarded, and cells that were loosely attached to the growing surface, were collected in PBS, as described in Example 2B. These cells were washed and resuspended in TBS, and were regarded as advanced apoptotic cells. Equal numbers of apoptotic or control non-treated cells ($10^5$) in a volume of 100 $\mu$l, were mixed with 100 $\mu$l of 25 mM of $CaCl_2$ and the clotting time was measured. Mean clotting time in he presence of the control, non-apoptotic cells was 78 sec. (±1.4; SD). The apoptotic cells were highly procoagulant, shortening clotting time to 38.0±2.8 sec. These results demonstrate that apoptotic cells are highly procoagulant. Inhibition of their procoagulant activity by NST300 compounds was tested following pre-incubation of apoptotic cells with the different NST300 compounds.

Pre-incubation of equal numbers of apoptotic or control non-treated cells ($10^5$) with NST300 compounds was for 10 minutes at room temperature in a final volume of 100 $\mu$l. The compounds were used at concentration of 0.5 $\mu$M. The results can be seen in FIG. 5a. The addition of NST301 or of NST302 compounds at a concentration of 0.5 $\mu$M to apoptotic cells increased the clotting time by a factor of 2, and corrected the procoagulant effect of the apoptotic cells, thus demonstrating the potential of NST300 compounds as potent inhibitors of this effect of apoptotic cells.

Conversely, the control peptide (NST301-C) had only a mild effect on the clotting time in the presence of apoptotic cells.

NST 302 as a Potent Inhibitor of Apoptotic-cell-mediated Thrombin Generation.

One of the final steps of both intrinsic and extrinsic pathways of coagulation, is the generation of thrombin from prothrombin. Thrombin is the final protease generated in the sequence of coagulation reaction, and its activity entails conversion of fibrinogen to fibrin, that forms the clot. Generation of thrombin on the pro-coagulant surface of apoptotic cells was assayed (according to Bombeli T. et al., 1997, Blood 89(7), 2429–2442), by determining its activity, using the chromogenic substrate S-2366 (from Chromogenix, Sweden). Samples of pro-coagulant cells (HeLa cells treated with 500 $\mu$M of DA for 18 hours) were used for the assay. Reaction mixture, in a plastic 1 ml cuvette, contained 100 $\mu$l of cells (1.5×$10^5$), 350 $\mu$l of HBS (150 mM NaCl, 10 mM (Hepes pH 7), and 150 $\mu$l of normal control plasma, recalcified with 300 $\mu$l of 25 mM $CaCl_2$. The substrate S-2366 was added to a final concentration of 0.2 mM, and the kinetics of thrombin activity was determined by optical density at $OD_{405}$. Data was collected and analyzed by the Swift kinetics software (Pharmacia). As shown in FIG. 5b, thrombin activity (reflecting thrombin generation) of apoptotic cells can be detected after one minute of addition of the chromogenic substrate, and the activity peaks after 3 minutes. 50% of the activity was achieved after 2 min. of substrate administration. NST302 compound was able to inhibit thrombin formation on the physiological surface of apoptotic cells (FIG. 5b). At concentrations between 5–25 $\mu$M, both the rate of thrombin activity and the lag time needed for activating the reaction were delayed, indicating that NST302 compound is able to compete with the formation of coagulation complex and to inhibit the number of complexes formed. At a concentration of 25 $\mu$M, the time needed to achieve 50% of thrombin activity was delayed by a factor of 2.25, and in the above experimental setting was 4.5 minutes. These results indicate that NST302 molecule can serve as an inhibitor of apoptotic-cell-mediated thrombin generation.

EXAMPLE 5

NST300 Compounds as a Diagnostic Kit for Early Detection of Apoptosis in Cultured Cells:

CMLA loss can be used for detection of apoptosis in cultured cells (Van Engeland, M et al., Cytometry 1998; 31:1–9). NST300 compounds bind to cells undergoing apoptosis. A diagnostic kit, based on this property, using NST300 compounds will thus be composed, for example, of the following:

1. Kit Reagents:

(Reagent #1 is the subject of this invention, the other reagents are used to support the reaction and will be prepared or supplied by commercial sources; specified concentrations and time periods are only given by way of examples and the kit is not limited by same)

1) NST300 compound at a stock solution concentration of 10 mM, with $X_5$ being linked: (I) to biotin
    (II) directly to fluorescein
2) Propidium iodide (PI) at a stock solution of 50 $\mu$g/ml.
3) Binding buffer 1: TBS-BSA, as described in Example 2.
4) Binding buffer 2: TBS.
5) PBS: Dulbecco's phosphate buffered saline.
6) fluorescent marker (FITC-labeled strepavidin) at a stock solution concentration of 50 ng/ml.
7) Fluorescent-compatible mounting reagent.

All reagents can be stored at 4° C.

Hereinafter are given protocols for performing tests with the above kit.

2. Protocols:

I. When NST Compound is Linked to Biotin
   a) Protocol for FACS-mediated Detection of Apoptotic Cells:
   The Protocol consists of the following steps:
   a. Adherent cells are grown and induced to undergo apoptosis by a trigger chosen by the user of the kit.
   b. Apoptotic cells are washed with PBS, rescued from places with a rubber policeman and resuspended in Binding buffer 1. Samples of 5×$10^5$ cells in a volume of 100 $\mu$l are taken for analysis.
   c. Cells grown in suspension can be used directly, following collection by centrifugation.
   d. Incubation of a sample for 60 minutes at room temperature with NST300 compound, at a concentration of 250 nM–750 nM, and with PI at a concentration of 5 $\mu$g/ml.
   e. Cells are collected by centrifugation (×100 g for 3 minutes) and washed 3 times in 500 $\mu$l of binding buffer 1.
   f. Cells are incubated in 100 $\mu$l of binding buffer 1 with the fluorescent marker (0.25 ng/ml)for 15 minutes in the dark.

g. Cells are washed in binding buffer 1 as specified in e., and are then taken for FACS analysis.

b) Protocol for in-situ Detection of Apoptotic Cells:

a. Cells are grown on class chamber slides at a density of $1 \times 10^5$ cells/chamber (preferably from Nunc), precoated with 1% gelatin.
b. Apoptosis is induced by a trigger chosen by the user of the kit.
c. Slides are then washed with binding buffer 2 and resuspended in 100 ul of same buffer.
d. Slides are then incubated with NST300 compound at a concentration of 250 nM–750 nM for 60 minutes at room temperature.
e. Step c. is then repeated.
f. Slides are incubated with the fluorescent marker at a concentration of 0.25 ng/ml for 15 minutes in the dark.
g. A drop of fluorescent-compatible reagent and a coverslip are added onto the cells of each slide.
h. Slides are ready to be viewed by fluorescent microscopy using a filter for FITC.

c) Protocol for Detection of Apoptosis in a Microtiter Plate:

For usage of this protocol, all manipulations of cells may be performed in a microtiter plate, provided that a microtiter-plate centrifuge adapter is available. The additional reagents need to be supplied by the user o the kit:

(1) Sterptavidin, conjugated to horseradish peroxidase (HRP) (preferably from Jackson ImmunoReasearch Lab Inc.)
(2) O-phenylenediamine (OPD) dihidrochloride (preferably from Sigma), prepared for use according to manufacturer's instructions.
(3) 4N HCl Working Protocol (a) Adherent cells are cultured in 24–96 wells plates, at a density of $2.5-7 \times 10^4$ cells/well.
(b) Apoptosis is induced by a method chosen by the user of the kit. Non-treated cells serve as control for determination of background binding.
(c) The medium is discarded, and cells are washed in binding buffer 2.
(d) A solution containing NST300 compound at a concentration of 250 nM–750 nM is then added (in a volume of 100–300 µl) and the plate is incubated for 60 minutes at room temprature.
(e) Step (c) is repeated.
(f) A solution of sterpatavidin-conjugated HRP is then added, at a dilution of 1:10,000 in PBS, in a volume of 100–300 µl. Incubation is of 45 minutes at room temperature.
(g) Step (c) is repeated.
(h) OPD substrate is added to each well (in a volume of 100–300 µl). As soon as a yellow color is developed, the reaction is terminated with 50 µl of 4N HCl.
(i) Plates are read in a slate reader, at 405 nm.

The amount of the yellow color developed is proportional to the amount of NST300 compound bound to apoptotic cells.

The values obtained with non-apoptotic cells serve as a background.

II. When NST Compound is Directly Linked to Fluorescein

In case of a direct linkage of NST300 to fluorescein, the use of a separate fluorescent marker is eliminated from the protocol. Therefore, in case of detection of apoptosis by FACS, steps e and f are eliminated. In case of in-situ detection of apoptosis, steps e and f of the respective protocol are eliminated.

EXAMPLE 6

NST 302 Compound Competes with Plasma of Patients with Systemic Lupus Erythematasus (SLE) (Lupus Plasma) for Binding to PS Exposing Surfaces.

The antiphospholipid antibody syndrom (APS) is a thrombophilic condition, characterized by a panel of antibodies that recognize anionic phospholipid-protein cofactor complexes. The antiphospholipid antibodies lupus anticoagulant and anticardiolipin, (present in high concentrations in SLE patients), are associated with several medical disorders including artherial and venous thrombosis, and recurrent pregnancy loss (Rand J H et al., 1998, Blood. 92, 1652–1660). Since the NST300 compounds are capable of binding co anionic phospholipids, their ability to compete with plasma derived from SLE patient for binding to anionic phospholipid presenting surfaces was tested. Two types of targets were chosen for binding:

(A). Noncellular Negatively Charged Phospholipid Coated Surface (Cardiolipin)
(B). Physiological Surface of PS Presenting Cells Such as BeWo trophoblast Cell Line or HUVEC Cells.

The results of these experiments are described hereafter:

(A). Competition Between NST 302 Compound and Lupus Plasma; Low Concentrations of NST 302 Inhibits Binding of Lupus Plasma to CL.

Cardiolipin (CL), a negatively charged phospholipid, was used to demonstrate binding of Lupus plasma to anionic phospholipids in ELISA assays that were performed according to Hazeltine et al., 1988 J. Rheumatology 15, 80–86.

CL, (Diphosphatidylglycerol, c-1649, Sigma), prepared at 50 µg/ml in ethanol, was added to a 96 well plate (100 ul/well) using Immunolon 4 plates (Dynatech, Chantilly, Va.) and incubated for 16–20 hr for evaporation or ethanol. As control, wells were coated with ethanol only. The coated plates were washed 3 times with 100 ul of blocking buffer (PBS containing 0.3% gelatin (Sigma) and 1 mM EDTA) to block non specific binding. A 5 min incubation time was used between each wash. Normal plasma (Ilex, Italy, 84670-11) and Lupus plasma (either from Gradipore, Australia, LAHP-1, or from Biopool, Ventura, Calif.) were prepared according to the producer instruction. The plasma was diluted 1/10 in the blocking buffer and was added to the CL and ethanol coated wells. Binding of different NST 300 compounds to CL was performed by addition of serial dilutions of NST compounds (prepared in the plasma/blocking buffer solution) to the CL or ethanol coated wells. Following 3 hr incubation, the plates were washed twice with PBS/BSA buffer (0.4% bovine serum albumin (BSA) in PBS). For detection of anticardiolipin binding property of the tested plasma, the plates were incubated with a 1/10000 dilution of Peroxidase-conjugated affinity purified Goat anti-human IgG (Jackson Immunoresearch lab.) in PBS/BSA buffer for 1 hour. The plates were then washed 3 times with PBS/BSA buffer, and color reaction was developed by incubation with 100 ul of 0-phenylenediamine (OPD) dihydrochloride (Sigma p-7288) at a concentration of 0.4 mg/ml in 0.05 M phosphate citrate buffer, pH 5.0 supplemented, with 4 ul of 30% hydrogen peroxide (Aldrich) for 10 ml mixture. To detect the level of NST 300 compound that was bound to CL, parallel wells were incubated with streptavidin conugated to OPD (SA-OPD, Jackson Immunoresearch lab.), that specifically recognize the biotinylated NST 300 compound. The resulting colour changes were recorded at 405 nM using a Bio Tek Elx800 Eliza reader.

FIGS. 6a and 6b demonstrate that binding of NST302 compound to CL is concentration dependent, and reached a saturation at about 0.3 µM. No significant effects were observed in the total binding of this compound in the presence of either Lupus or normal plasma (FIGS. 6a and 6b). FIG. 6a represent binding of plasma (derived from a pool of either normal or SLE patients) to CL coated ELISA wells, expressed as an optical density units. High levels of binding, can be observed in the presence of Lups plasma (commercially available from Gradipore) but not in the presence of normal plasma, reflecting the presence of anti CL antibodies in the Lupus plasma. However, in the presence or low concentrations of NST302 compound, displacement of the binding of Lupus plasma to CL is evident, starting from 0.1 $\mu$M and reaching its maximum effect at 2.5 $\mu$M (FIG. 6a). When a similar experiment using plasma derived from a different pool of SLE patients (commercially available from Biopool Inc.) was performed (FIG. 6b), similar results were obtained. These results further exemplify the specific displacement of Lupus plasma from CL by the NST 302 compound and suggest the future use of NST302 as a competitive inhibitor that will lower the pro-thrombotic risks associated with binding of anti phospholipid antibodies to negatively charged surfaces.

B. NST302 Inhibits Binding of Anti β2PI Antibodies to Cardiolipin.

Antiphospholipid antibodies (APLA) comprise a family of antibodies characterized by their reactivity with negatively charged phospholipids in vitro. The target or many anti-phospholipid antibodies is either a complex between anionic phospholipid and the plasma protein Apolipoprotein-H (β2GPI) or the protein β2GPI alone bound to PS (McNeil et al., 1990, Matsurra et al., 1994). The ability of NST302 to interfere with binding of anti β2GPI antibodies to CL was tested in ELISA assay. The assay was performed as essentially described above for anti CL ELISA with several modifications. The CL or ethanol coated wells were incubated with normal plasma (Ilex) or normal plasma supplemented with a 1/500 dilution of goat anti-human β2GPI (Affinity biologicals, Canada) Serial dilutions of NST302 compound were prepared in the plasma/blocking buffer solution, and added to the wells. Following washes, the wells were incubated for 1 hour with 1/10000 of Peroxidase-conjugated affinity purified rabbit anti goat IgG (Jackson Immunoresearch lab. PA) in PBS/BSA buffer. Washes and development were as described for anti CL ELISA. In the following experiments, CL coated wells were incubated with 1/500 dilution or affinity purified goat anti-human β2GPI in 10% normal plasma (as a source for β2GPI protein and buffering condition). In the absence of NST302 compound, binding of anti β2GPI to CL is demonstrated (FIG. 6c). However, in the presence of 0.1–50 $\mu$M of NST 302, a significant displacement of anti β2GPI from CL could be seen. A complete inhibition of anti β2GPI binding is evident at 50 $\mu$M, suggesting that NST302 binds with high affinity to CL (FIG. 6c) These results emphasize the potency of NST302 to compete and subsequently to displace binding of APLA and particularly anti β2GPI antibody subtypes from binding to CL.

C. NST302 Inhibits Binding of Anti β2GPI to HUVEC Cells.

Human β2GPI is a plasma phospholipid binding protein that is required for the binding of autoantibodies in sera from patients with APS to cardiolipin (McNeil H P et al. , 1990 Proc. Natl. Acad. Sci. 87, 4120–4124) The β2GPI protein binds also to PS presenting cells (Yan W Y et al., 1996, Lupus, 5, 504.) and to activated platelets (Nimpf J E et al. , 1987, Biochem. Biophis. Acta, 884, 142), and exhibit anticoagulant properties. Anti β2GPI antibodies are present in sera of APS patients. Therefore, the ability of the NST302 compound to interfere with the binding of anti βGPI to PS presenting cells was tested in a modified ELISA assay, and is demonstrated here in FIGS. 6d and 6e. For cell-ELISA tests, HUVEC cells or BeWo cells (both at 40,000/well), were plated on 96 well tissue culture plates (Nunc) in 200 ul of the culture medium, and allowed to grow for 18–22 hours. Following 2 washes with Hepes buffer (10 mM Hepes pH, 8, 140 mM NaCl) and 5 min incubation with the culture medium, the wells were incubated for 3 hr with 10% of normal plasma in PBS (as a source of β2GPI protein), supplemented with 1/500 of goat anti-human Apolipoprotein-H (β2GPI) (Affinity Biologicals, Pa.) Parallel control wells were incubated with 10% of normal plasma from Ilex. Serial dilutions of NST compounds were prepared in plasma/PBS. Washes and development were as described for anti CL ELISA.

As presented in FIGS. 6d and 6e, only residual binding of βGPI to HUVEC or BeWo cell's surface is observed. In the presence of plasma and absence of NST302, these cells support binding of anti β2GPI to their surface. However, displacement of anti β2GPI by NST302 compound in this system occurred in a concentration dependent manner, similar to the results obtained with CL and reached its maximum effect at a concentration of 50 $\mu$M of the compound. These data therefore demonstrate, that NST302 compound can serve as a competitive inhibitor for binding of anti β2GPI that is present in sera of Lupus patients to physiological surfaces, and lower the pro-thrombotic risks associated with binding of anti phospholipid antibodies to negatively charged surfaces.

EXAMPLE 7

NST 302 Compound Can Detect Apoptotic Cells In-vivo

Since the original description of apoptosis by Kerr in 1972 (Kerr J. F et al; 1972, Brit J. Cancer 26, 239–257) its assessment in vivo has required direct examination or biopsied or aspirated material. A technique capable of localizing and quantifying apoptosis in vivo would permit assessment of apoptosis-related disease progression or regression and similarly define the efficacy of therapy designed to inhibit or induce cell death.

In order to demonstrate the potential use of NST 300 compounds as in-vivo detector of apoptotic process, we have used an animal model of induction of hepatic apoptosis in mice by the anti Fas antibody. The Fas protein, encoded in the mouse by the gene fas, is a cell surface antigen of about 35 kDa that mediates apoptosis (Nagata S. et al, 1995, Science 267, 1449–1456) and is expressed in a variety of tissues including liver, heart, lung, ovary, kidney and thymus. Fas has been shown to trigger apoptosis in susceptible target cells when bound to its physiological ligand (FasL) (Suda T. et al; 1994, J. Exp. Med. 179, 873–879), or to agonistic anti-Fas antibodies (Itoh N. et al, 1991, Cell, 66, 233–234). In-vivo treatment of mice with an anti-Fas monoclonal agonistic antibody induces early and massive apoptosis of hepatocytes, leading to the death of the animal within few hours. The sequence of the pathological changes are similar to those found in acute liver failure due to hepatitis viruses infection or toxins in humans. In the current study, we have used the NST302 compound that was coupled to biotin. We performed immunohistochemical analysis with NST302 to determine its ability to detect in vivo sites of apoptotic cell death occurring in Fas-mediated hepatocyte apoptosis. Such in vivo studies may prove useful in a clinical setting for noninvasive diagnosis, monitoring of disease progression or regression, and determining efficacy of treatment.

A. Murine Model of Fas-Mediated Apoptosis

Massive hepatic apoptosis can be induced within 1–2 hr in mice following intravenous injection of anti-Fas antibody (Ogasawara J. et al, 1993, Nature 364, 806–809). We have used this well described model of in-vivo programmed cell death to test the specific localization of NST302 to an organ undergoing apoptosis in vivo. Five-weeks-old male BALB/c mice were injected intravenously with 10 μg/animal of purified hamster anti-Fas mAb (Jo2, PharMingen, San Diego, Calif.) using the model described by Ogasawara et. al. (1993, Nature 364, 806–809). Mice were then injected intravenously with 5 μM of NST302. Injections were performed at different time intervals between 5 min-2 hr after antibody treatment. Two different types of control animals were used: animals injected with NST302 only, and animals treated with the anti-Fas antibodies only. All animals were killed 2 hr after administration of antibody followed by organ removal. Heart, lung and liver were collected. Liver were sectioned transversely across the mid-portion of each lobe; organs were fixed in phosphate-buffered formalin for histological and immunohistochemical analyses. Severe histological lesions of the liver were observed in treated mice, including morphological changes typical of apoptosis. Sections of liver from mice treated with the anti-Fas antibody showed a morphologically well defined sequence of events characteristics of apoptosis (margination of chromatin, pyknosis, and karyorrhexis) changes were also focally associated with hemorrhage (peliosis) (FIGS. 7b and 7d) in the entire lobule. Evidence of apoptosis were provided by several parameters: the first is the morphological structure of the cell and nuclei stained with Hematoxylin/Eosin indicated that apoptotic injury has been observed in 80–90% of all hepatocytesas shown in FIG. 7b as compared to control non-treated animal shown in FIG. 7a. The second is by the number of TUNEL-positive cells that represented approximately 50%. of hepatocytes after 2 hours (FIG. 7b as compared to control animal in FIG. 7c) The absence of inflammatory cells was consistent with the non inflammatory nature of the apoptotic cell death. No evidence of apoptotic cells was observed when liver sections from control animals injected with NST302 alone were seen (not shown). Similar results were obtained when animals were injected with PBS alone (data not shown). Histological analysis were performed with other organs (heart and lung), and no apoptotic or necrotic cells were observed after injection of the antibody (no shown).

B. Staining of Apoptotic Cells with NST302

Animals that were subjected to induction of apoptosis by the Fas antibodies were used for staining with NST300 compound in order to evaluate the ability of NST302 compound to label apoptotic cells in-vivo. Formalin fixed paraffin-embedded tissues were sectioned (5 μm) for staining with Hematoxylin/Eosin or other techniques.

Endogenous peroxidase activity was blocked by incubation with 3% $H_2O_2$.

Sections were washed in phosphate buffered saline (PBS). Bound NST302 was visualized using the avidin biotin complex method with horse-radish peroxidase conjugated avidin [DAKO® Catalyzed Signal Amplification (CSA) System, and Peroxidase (#K1500, DAKO corporation, Calif. USA)] at room temperature. After washing with PBS, staining was developed with 3,3-diaminobenzidine tetrahydrochloride (DAB), and counterstained with Hematoxylin.

For the detection of apoptotic nuclei, sections were stained using the ApopTag® Plus Peroxidase In Situ apoptosis detection Kit (#S7101-KIT, Appligene ONCOR, Md. USA) labeling of apoptotic cells is based on modifying genomic DNA using terminal deoxynucleotidyl transferase (TdT), and detection of positive cells is done by specific staining.

Histological Examination

Liver sections from different lobes were used for detection of stained apoptotic cells compared to normal cells. Using light microscopy (x400), twenty fields of stained cells were evaluated.

The percentage of apoptotic cells in the fields was estimated by evaluating parallel sections stained with Hematoxylin/Eosin. Analysis was performed blindly, since the pathologist performing the histological evaluation was unaware of the assignment of mice to the treatment or control group.

NST362 staining (brown immunostaining product) was observed at cytoplasma and cytoplasmatic border of apoptotic hepatocytes (FIGS. 8b and 8d) as compared to sections from animals injected with NST302 only (FIGS. 8a and 8c). Although this result was focal, the localization pattern is consistent with phosphatidylserine (PS) externalization, and staining was never observed in normal hepatocytes (FIGS. 8a and 8c) The same pattern of staining appeared when Annexin V (a protein that strongly binds to PS containing membranes) was exogenously added to the apoptotic cells (data not shown). These experiments indicate that exposure of PS on the surface of cells undergoing apoptosis can be detected in-vivo with the NST300 compound in as animal model such as Fas-mediated fulminant hepatitis.

C. Pharmacokinetic Studies

While dealing with a biological compound that is destined to be used for diagnostic purposes, the time course that the compound is detectable in the body should be considered. Pharmacokinetics appearance and disappearance of the compound NST302 was examined in the following time intervals: 5, 15, 20, 30, 60, 90, 120 min after injection of the compound (FIG. 9). Five minutes after the injection of NST302, early distribution of the compound, was observed both in animals treated (FIG. 9a) or untreated with anti-Fas antibody (data not shown) The peak of the staining appeared after 15 and 20 minutes from injection of the NST302 compound (FIG. 9b and 9c), and then slowly declined (FIGS. 9d–9g). Two hours after the injection of the compound no staining was found (FIG. 9g) The above results indicate that the NST302 is a suitable compound for diagnostic purposes due to its ability to significantly differentiate apoptotic cells from normal cells and its convenient time of clearance from the detected organs.

---

What is claimed is:

1. An NST300 compound capable of selectively binding to membranes upon CMLA loss of the general formula I comprising the following components:

$$X_1\text{—}[(X_3)_a/(X_4)_b]$$

wherein:

$X_1$ stands for a saturated or unsaturated fatty acid residue comprising 6–20 carbon atoms; or a cysteine residue bound through a thioether bond to a prenyl group comprising 5–20 carbon atoms; said residue being linked to the adjacent component of the compound through an amide bond;

$X_3$ comprises 1–6 amino acids, of which 1–6 are positively charged, the other amino acid residues being polar uncharged amino acids; and $X_4$ comprises 1–6 amino acids, of which 1–2 are aromatic amino acids, the other amino acids being selected among polar uncharged amino acids and hydrophobic amino acids;

wherein:

a stands for an integer of 1–8;

b stands for an integer of 1–8; and $(X_3)_a$ comprises at least 6 positively charged amino acids;

the groups $X_3$ and $X_4$ being located at various places in the compound, wherein the compound is capable of binding to a cell membrane having a loss of cell membrane lipid asymmetry (CLMA).

2. A compound according to claim 1, wherein $X_1$ is a residue of a saturated fatty acid of formula $CH_3(CH_2)_nCO_2H$, in which n stands for an integer of 5–15; or for a cysteine residue bound through a thioether bond to a prenyl group of 5–20 carbon atoms.

3. A compound according to claim 2, wherein $X_1$ is selected among myristic acid and palmitic acid; and farsenyl cysteine.

4. A compound according to any one of claims 1 to 3, wherein the positively charged amino acids of $X_3$ are selected among lysine, arginine, histidine or any amino acid which is comprised of a positively charged group covalently bound to an α-carbon atom or to an α-amine on a peptide backbone by a spacer selected from a group consisting of an alkene of 2–4 carbon atoms and combinations thereof.

5. A compound according to claim 4, wherein the positively charged amino acids in $X_3$ are selected among lysine and arginine and combinations thereof.

6. A compound according to any one of claims 1 to 3, wherein the polar uncharged amino acids of $X_3$ are selected among serine, threonine, asparagine and glutamine and combinations thereof.

7. A compound according to any one of claims 1 to 3, wherein the aromatic acids of $X_4$ are selected among phenylalanine and tryptophan and combinations thereof.

8. A compound according to any one of claims 1 to 3, wherein the polar uncharged amino acids of $X_4$ are selected among serine, asparagine and glutamine and combinations thereof.

9. A compound according to any one of claims 1 to 3, wherein the hydrophobic amino acids of $X_4$ are selected among leucine and alanine and combinations thereof.

10. A compound according to any one of claims 1 to 3, which comprises additional groups $X_2$, $X_5$ and $X_6$ and which has the general formula Ia comprising the following components:

$$X_1\text{—}X_2\text{—}[(X_3)_a/(X_4)_b/(X_5)_c]\text{—}X_6$$

wherein:
$X_2$ is selected among 0–3 glycine residues and 0–2 β-amino alanine molecules;
$X_5$ is a compound of general formula II

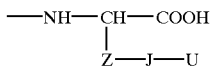

wherein Z stands for a spacer group selected among an alkane containing 1–4 carbon atoms and an alkene containing 2–4 carbon atoms, J stands for a functional group selected among amines, thiols, alcohols, carboxylic acids, esters, aldehydes and alkyl halides; U is a labeling group;
c standing for 0–10; and
$X_6$ being 0; or being a saturated or unsaturated fatty acid residue comprising 6–20 carbon atoms; or a cysteine residue bound through a thioether bond to a prenyl group comprising 5–20 carbon atoms;
within the subunit $[(X_3)_a/(X_4)_b/(X_5)_c]$ the groups $X_3$, $X_4$ and $X_5$ being located at various places.

11. A NST300 compound of the general formula Ia comprising the following components:

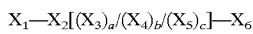

wherein:
$X_1$ stands for a saturated or unsaturated fatty acid residue comprising 6–20 carbon atoms; or a cysteine residue bound through a thioether bond to a prenyl group comprising 5–20 carbon atoms; said residue being linked to the adjacent component of the compound through an amide bond;
$X_2$ is selected among 0–3 glycine residues and 0–2 β-amino alanine molecules;
$X_3$ comprises 1–6 amino acids, of which 1–6 are positively charged, the other amino acid residues being polar uncharged amino acids;
$X_4$ comprises 1–6 amino acids, of which 1–2 are aromatic amino acids, the other amino acids being selected among polar uncharged amino acids and hydrophobic amino acids;
$X_5$ is a compound of general formula II

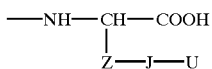

wherein Z stands for a spacer group selected among an alkane containing 1–4 carbon atoms and an alkene containing 2–4 carbon atoms, J stands for a functional group selected among amines, thiols, alcohols, carboxylic acids, esters, aldehydes and alkyl halides; U is a labeling group; and
$X_6$ being 0 or a saturated or unsaturated fatty acid residue comprising 6–20 carbon atoms; or a cysteine residue bound through a thioether bond to a prenyl group comprising 5–20 carbon atoms; wherein:
a stands for an integer of 1–8;
b stands for an integer of 1–8; the groups $X_3$ and $X_4$ being located at various places in the compound;
c stands for 0–10; such that within the subunit $[(X_3)_a/(X_4)_b/(X_5)_c]$
$(X_3)_a$ comprises at least 6 positively charged amino acids and the groups $X_3$, $X_4$ and $X_5$ being located at various places, wherein U is a labeling group for specific binding selected among biotin and a group containing a substituent selected among a fluorescein, a radioisotope and a paramagnetic contrast agent.

12. A compound according to claim 11, wherein the fluorescein is fluorescein isothiocyanate.

13. A compound according to claim 11, wherein the radioisotope is selected among technetium, lead, mercury, thallium and indium.

14. A compound according to claim 11, wherein the paramagnetic contrast agent is a paramagnetic metal ion chelate.

15. A compound according to claim 11, wherein $X_5$ is a lysine residue being substituted at the ε-amino group by said labeling group.

16. A compound according to claim 11, wherein $X_6$ is a cysteine residue bound through a thioether bond to a prenyl group, wherein the cysteine carboxyl group can be either free or methylated.

17. Myristate-GGGKKKKKRFSFKKSFKLSGFS-FKKNKKK (SEQUENCE ID NO. 1)-U, in which G=glycine, K=lysine, R=arginine, F=phenylalanine, S=serine, L=leucine, N=asparagine and U is a labeling group for specific binding selected among biotin and a group containing a substituent selected among a fluorescein, a radioisotope and a paramagnetic contrast agent.

18. Myristate-GGGKKKKKRFSFKKSFKLSGFS-FKKNKK-K (SEQUENCE ID NO. 1)-(biotin), wherein G=glycine, K=lysine, R=arginine, F=phenylalanine, S=serine, L=leucine, N=asparagine.

19. Myristate-KKKKKRFSFKKSFKLSGFSFKKNKKK (SEQUENCE ID NO. 2)-U, wherein G=glycine, K=lysine, R=arginine, F=phenylalanine, S=serine, L=leucine, N=asparagine and U is a labeling group for specific binding selected among biotin and a group containing a substituent selected among a fluorescein, a radioisotope and a paramagnetic contrast agent.

20. Myristate-KKKKKRFSFKKSFKLSGFSFKKNKKK (SEQUENCE ID NO. 2)-(biotin), wherein G=glycine, K=lysine, R=arginine, F=phenylalanine, S=serine, L=leucine, N=asparagine.

21. A compound according to claim 14, wherein the paramagnetic metal ion chelate is gadolinium-diethylenetriaminepentaacetic acid (Gd-DTPA).

22. A pharmaceutical composition comprising as active ingredient an NST300 compound according to any one of claims 1 to 3.

23. A pharmaceutical composition according to claim 22 which comprises a pharmaceutically acceptable carrier.

24. A pharmaceutical composition according to claim 23, wherein the carrier is selected among suitable solvents; and the composition further comprises emulgators, excipients, talc, flavors, and colors.

25. A pharmaceutical composition according to claim 22, which is in a form selected among tablets; capsules; solutions; and emulsions.

26. A pharmaceutical composition according to claim 22, further comprising an additional pharmaceutically active compound.

27. A method for the treatment or prevention of prothrombic states in disorders associated with excessive procoagulant activity initiated or propagated by CMLA loss comprising administering a pharmaceutically acceptable amount of the NST300 compound of any one of claims 1–3.

28. The method according to claim 27, wherein the disorders are arterial or venous thrombosis; sickle cell disease; thalassemia; antiphospholipid antibody syndrome; lupus erythematosus; shed membrane particles and apoptosis.

29. A method for the treatment or prevention of prothrombic states in disorders associated with excessive procoagulant activity initiated or propagated by CMLA loss comprising administering a pharmaceutically acceptable amount of the compounds of any one of claims 17–20.

30. A method according to claim 29, wherein the disorders are arterial or venous thrombosis; sickle cell disease; thalassemia; antiphospholipid antibody syndrome; lupus erythematosus; shed membrane particles and apoptosis.

31. A method for the diagnosis of CMLA loss comprising administering a pharmaceutically acceptable composition including the NST300 compound of any one of claims 1–3.

32. The method according to claim 31, wherein the pharmaceutically acceptable composition includes a diagnostic agent for the detection and imaging of cell death.

33. The method according to claim 32, wherein the pharmaceutically acceptable composition includes a diagnostic agent for the detection and imaging of apoptosis.

34. The method according to claim 31, wherein the pharmaceutically acceptable composition includes a diagnostic agent for thrombosis or for prothrombotic states.

35. The method according to claim 31, wherein the pharmaceutically acceptable composition includes a diagnostic agent for pathophysiological states associated with apoptosis.

36. The method according to claim 35, wherein the pharmaceutically acceptable composition is employed as a diagnostic agent for monitoring of response to anti-cancer treatments, for diagnosis of disorders of inappropriate excessive apoptosis, for monitoring of response to cytoprotective treatments or for monitoring of graft survival following organ transplantation.

37. A diagnostic kit comprising a NST300 compound according to any one of claims 1 to 3.

38. A method for targeting drugs to tissues inflicted by CMLA loss comprising administering a pharmaceutically acceptable composition including a target drug conjugated with the NST300 compound of any one of claims 1–3.

39. A method for targeting drugs to tissue in the body which are inflicted by CMLA loss comprising conjugating through an esteric bond an NST300 compound of any one of claims 1–3 with a drug to be targeted.

40. A process for the preparation of a NST300 compound of the general formula I according to any one of claims 1 to 3 comprising the following steps:

a. for the preparation of the sub unit $[(X_3)_a/(X_4)_b]$, loading an α-amine protected, c-terminal amino acid of said sequence on a solid support, removing the α-amine protecting group, and sequentially preparing the peptide sequence;

b. for coupling of $X_1$, removing the α-amino protecting group from the N-terminal amino acid, and then introducing $X_1$ into the peptide-resin under the same conditions as in step a.; and c. finally cleaving the peptide from the solid support, purifying the peptide and characterizing the peptide.

41. A process for the preparation of a NST300 compound of the general formula Ia according to claim 10 comprising the following steps:

a. for the preparation of the sub unit $[(X_3)_a/(X_4)_b/(X_5)_c)]$, loading an α-amine protected, c-terminal amino acid of said sequence on a solid support, removing the α-amine protecting group, and sequentially preparing the peptide sequence;

b. for coupling of $X_1$, removing the α-amino protecting group from the N-terminal amino acid, and then introducing $X_1$ into the peptide-resin under the same conditions as in step a.; and c. finally cleaving the peptide from the solid support, purifying the peptide, and characterizing the peptide.

42. A process for the preparation of a NST300 compound of the general formula Ia according to claim 10 comprising the following steps:

a. for the preparation of the sub unit $[(X_3)_a/(X_4)_b/(X_5)_c)]$, loading an α-amine protected, c-terminal amino acid of said sequence on a solid support, removing the α-amine protecting group, and sequentially preparing the peptide sequence;

b. for coupling of $X_1$, removing the α-amino protecting group from the N-terminal amino acid, and then introducing $X_1$ into the peptide-resin under the same conditions as in step a.; and c. finally cleaving the peptide from the solid support, purifying the peptide, and characterizing the peptide, wherein preparation of $X_5$ and its coupling to a labeling group or to $X_6$ comprises loading an orthogonally protected amino acid on a solid support, selectively removing the protecting group on an ω-functional group, and introducing $X_6$ or the labeling group of $X_5$ into the amino acid-resin by using an appropriate coupling reagent or by using a pre-activation method.

43. A process according to claim 42, wherein the coupling agent is HBTU/HOBT.

44. A process according to claim 42, wherein the pre-activation method is the formation of an ester, azide or an anhydride.

45. A process for the reparation of a NST300 compound of the general formula Ia according to claim 10 comprising the following steps:

a. for the preparation of the sub unit $[(X_3)_a/(X_4)_b/(X_5)_c)]$, loading an α-amine protected; c-terminal amino acid of said sequence on a solid support, removing the α-amine protecting group, and sequentially preparing the peptide sequence;

b. for coupling of $X_1$, removing the α-amino protecting group from the N-terminal amino acid, and then introducing $X_1$ into the peptide-resin under the same conditions as in step a.; and c. finally cleaving the peptide from the solid support, purifying the peptide, and characterizing the peptide, wherein step a is also used for the integration of $X_5$, coupled either to a labeling group or coupled to $X_6$, into the peptide sequence.

46. A process according to claim 42, wherein the characterizing is performed by HPLC-MS.

47. A method for selectively targeting a medicinally-useful agent to cells that have undergone CMLA loss, within a region of mammalian subject, comprising administering to said cells said medicinally-useful agent wherein said agent comprises the compound of formula I, said compound comprising the following components:

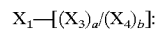

wherein:

$X_1$ stands for a saturated or unsaturated fatty acid residue comprising 6–20 carbon atoms; or a cysteine residue bound through a thioether bond to a prenyl group comprising 5–20 carbon atoms; said residue being linked to the adjacent component of the compound through an amide bond;

$X_3$ comprises 1–6 amino acids, of which 1–6 are positively charged, the other amino acid residues being polar uncharged amino acids; and $X_4$ comprises 1–6 amino acids, of which 1–2 are aromatic amino acids, the other amino acids being selected among polar uncharged amino acids and hydrophobic amino acids;

wherein:
a stands for an integer of 1–8;
b stands for an integer of 1–8; and $(X_3)_a$ comprises at least 6 positively charged amino acids and the groups $X_3$ and $X_4$ being located at various places in the compound, wherein the compound is capable of binding to a cell membrane having a loss of cell membrane lipid asymmetry (CLMA).

* * * * *